United States Patent [19]

Sibasaki et al.

[11] Patent Number: 4,839,388

[45] Date of Patent: Jun. 13, 1989

[54] PROSTACYCLINS AND PHARMACEUTICALS CONTAINING THE SAME

[75] Inventors: Masakatsu Sibasaki, Mitaka; Mikiko Sodeoka, Sagamihara; Katsuhiko Iseki, Abiko; Masaki Shinoda, Ibaraki; Chiyoko Aoki, Sagamihara; Yosio Hayasi, Ushiku; Toshiji Kanayama, Ibaraki, all of Japan

[73] Assignees: Mitsubishi Chemical Industries Limited; Sagami Chemical Research Center, both of Tokyo, Japan

[21] Appl. No.: 60,870

[22] PCT Filed: Sep. 18, 1986

[86] PCT No.: PCT/JP86/00486

§ 371 Date: May 18, 1987

§ 102(e) Date: May 18, 1987

[87] PCT Pub. No.: WO87/01696

PCT Pub. Date: Mar. 26, 1987

[30] Foreign Application Priority Data

Sep. 18, 1985 [JP] Japan .................. 60-204538

[51] Int. Cl.⁴ ............................. A61K 31/557
[52] U.S. Cl. ...................... 514/530; 514/63; 514/460; 514/569; 514/573; 514/621; 514/623
[58] Field of Search ............ 514/530, 573, 63, 460, 514/621, 623

[56] References Cited

U.S. PATENT DOCUMENTS

| | | | |
|---|---|---|---|
| 4,632,997 | 12/1986 | Shibasaki | 549/214 |
| 4,699,921 | 10/1987 | Shibasaki | 514/530 |

FOREIGN PATENT DOCUMENTS

| | | | |
|---|---|---|---|
| 136779 | 4/1985 | European Pat. Off. | 560/119 |
| 153822 | 9/1985 | European Pat. Off. | 560/119 |
| 57-145833 | 9/1982 | Japan | 514/530 |
| 59-82339 | 5/1984 | Japan | 514/530 |
| 59-137445 | 8/1984 | Japan | 514/530 |
| 61-129146 | 6/1986 | Japan | 514/530 |

OTHER PUBLICATIONS

Chemistry Letters, No. 4, Apr. 1986, pp. 559–562.

*Primary Examiner*—Robert Gerstl
*Attorney, Agent, or Firm*—Oblon, Fisher, Spivak, McClelland & Maier

[57] ABSTRACT

This invention relates to a novel prostacyclin represented by the formula:

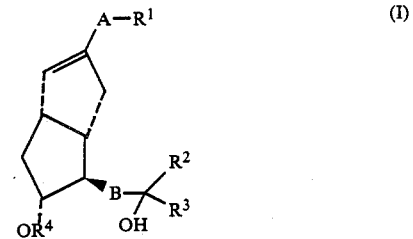

[wherein $R^1$ represents $-CO_2R^5$ group or $-CONR^6R^7$ group; A is
(i) $-CH=CH-CH_2CH_2-$ or
(ii) $-CH_2CH_2-O-CH_2-$;
B represents $-C\equiv C-$ group; $R^2$ represents an alkyl group, a cycloalkyl group, an alkenyl group, an alkynyl group, a phenyl group or a phenoxy group; $R^3$ represents a hydrogen atom, a methyl group or a vinyl group; $R^4$ represents a hydrogen atom, an acyl group, a tri(1 to 7 carbon atoms)hydrocarbyl-silyl group or a group forming an acetal bond with an oxygen atom of a hydroxy group; a double bond in the substituent represented by A is E or Z, or a mixture thereof; asymmetric center in the substituent represented by $R^2$ is an R-configuration or S-configuration, or a mixture thereof];

and uses in which they are employed as circulation ameliorating pharmaceuticals for blood flow ameliorating, antithrombus and the like, or antiulcer pharmaceuticals.

2 Claims, No Drawings

PROSTACYCLINS AND PHARMACEUTICALS CONTAINING THE SAME

[TECHNICAL FIELD]

This invention relates to novel prostacyclins and uses in which they are employed as crisulation ameliorating pharmaceuticals for blood flow ameliorating, antithrombus and the like, or antiulcer pharmaceuticals.

[BACKGROUND ART]

Prostacyclin (hereinafter written as $PGI_2$) has been known as a natural physiologically active substance and has the structure shown by the following formula:

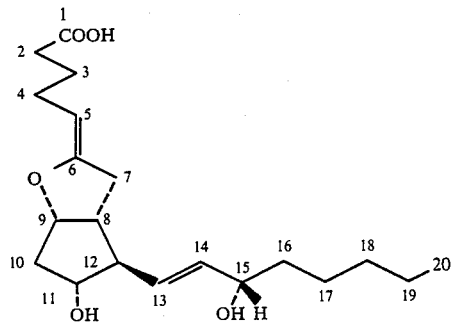

(II)

Its chemical name is (5Z,13E)-(9α,11α,15S)-6,9-epoxy-11,15-dihydroxyprosta-5,13-dienic acid. $PGI_2$ exists within the vascular walls and has the potent aggregation inhibiting effect of platelet as well as relaxing effect of smooth muscle of peripheral artery [Nature, 263, p. 663 (1976)].

$PGI_2$ exhibiting such effects is useful for prophylaxis and therapy of cerebral thrombosus, myocardial infarction and acute stenocardia induced by exasperation of platelet aggregation and further increase of thrombotic tendency, expected to be applicable for prophylaxis and therapy of arteriosclerotic diseases and desired to be developed as the so-called blood circulation ameliorating pharmaceuticals.

Also, prostaglandins containing $PGI_2$ are known to have gastric mucosa protective effect and blood flow increasing effect within gastric mucosa ['83 Inflammation Seminar "Prostaglandin" Pretext page 50 (Sponsored by Society of Inflammation of Japan)], and $PGI_2$ exhibiting such effects can be expected to be applicable for prophylaxis and therapy of gastrointestinal ulcers, typically stomach ulcer.

However, $PGI_2$ is a remarkably unstable substance and this has been an obstacle against practical application as pharmaceuticals.

In order to overcome such obstacle, studies have been made about stable analogues in which the oxygen atom between the carbon atoms at the 6- and 9-positions in $PGI_2$ is replaced with carbon atom. The carbacyclin type compounds [Japanese Provisional Patent Publication No. 130543/1979] shown by the formula (III) as represented by OP-41483 [Japanese Provisional Patent Publication No. 130543/1979] and 9(0)-methano-$\Delta^6 PGI_1$ represented by the formula (IV) [Japanese Provisional Patent Publication No. 32436/1981] are all chemically stable $PGI_2$ analogue compounds. Also, 9(0)-methano-$\Delta^{6(9\alpha)}$-$PGI_1$ (isocarbacyclin, formula (V)) in which the 5-position double bond in 9(0)-methano-prostacyclin (carbacyclin) is transferred to the 6(9α) position is also chemically sufficiently stable and has been reported as a $PGI_2$ analogue compound having potent physiological activities [Japanese Provisional Patent Publication No. 137445/1984].

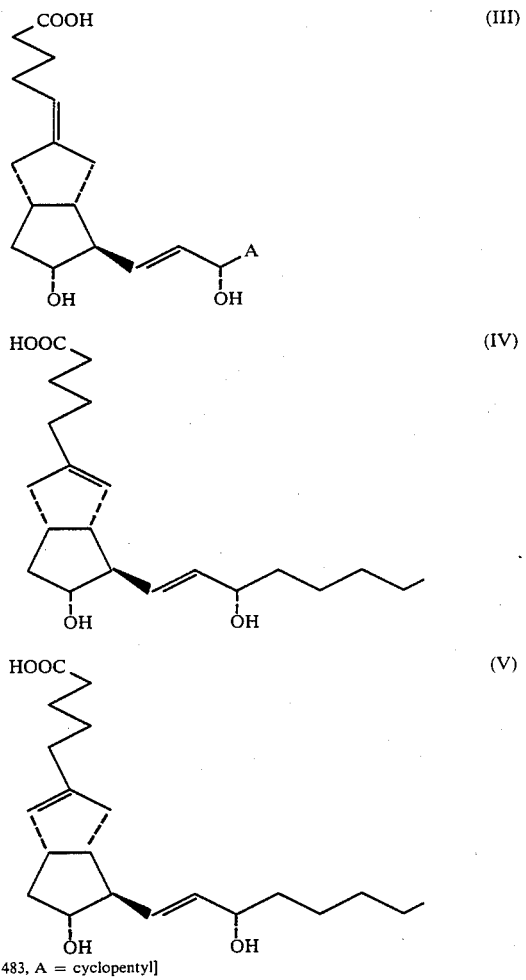

[OP-41483, A = cyclopentyl]

[DISCLOSURE OF THE INVENTION]

The present inventors have made extensive studies in order to provide prostacyclins which are stable, substantially free from decomposition at room temperature and have excellent pharmacological properties, and consequently created novel prostacyclins and found that said compounds have potent platelet aggregation inhibiting effect, hypotensive effect, vasodilative effect and antiulcer effect, and are also low in toxicity, to accomplish the present invention.

That is, the present invention concerns prostacyclins represented by the [I]:

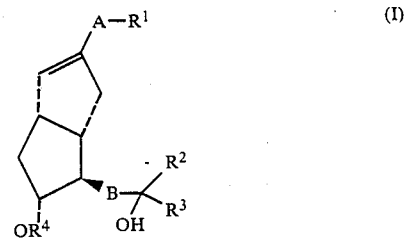

(I)

[wherein R¹ represents —$CO_2R^5$ group (in the group, $R^5$ represents a hydrogen atom, or a straight or branched alkyl group having 1 to 12 carbon atoms, or an aralkyl group having 7 to 12 carbon atoms, or a cycloalkyl group having 4 to 7 carbon atoms which may be unsubstituted or substituted by at least one alkyl group having 1 to 4 carbon atoms, or a substituted or unsubstituted phenyl group, or a monoequivalent cation), or —$CONR^6R^7$ group (in the group, $R^6$ and $R^7$ each may be the same or different, represents a hydrogen atom, an alkyl group having 1 to 10 carbon atoms, or a substituted or unsubstituted 5 -to 6-membered ring combined with nitrogen atom bonded thereto which may have further hetero atoms); A is (i) —CH=CH—$CH_2CH_2$— or
(ii) —$CH_2CH_2$—O—$CH_2$—;

B represents —C≡C— group; $R^2$ represents a straight or branched alkyl group having 3 to 10 carbon atoms, or a cycloalkyl group having 4 to 7 carbon atoms which may be unsubstituted or substituted by at least one alkyl group having 1 to 4 carbon atoms, or a straight or branched alkenyl group having 3 to 12 carbon atoms, or a straight or branched alkynyl group having 3 to 8 carbon atoms, or a substituted alkyl group having 1 to 3 carbon atoms which is substituted by a phenyl group or a phenoxy group which may be substituted, or an alkoxy group having 1–6 carbon atoms, or a cycloalkyl group having 5 to 8 carbon atoms; $R^3$ represents a hydrogen atom, a methyl group or a vinyl group; $R^4$ represents a hydrogen atom, or an acyl group having 1 to 7 carbon atoms, a tri(1 to 7 carbon atoms)hydrocarbylsilyl group or a group forming an acetal bond with an oxygen atom of a hydroxy group; a double bond in the substituent represented by A is E or Z, or a mixture thereof; asymmetric center in the substituent represented by $R^2$ is an R-configuration or S-configuration, or a mixture thereof.]. Also, it relates to a pharmaceuticals having circulation ameliorating effect and antiulcer effect and comprising those prostacyclins or non-toxic salt of its acid, or their cyclodextrin-inclusion compound as an active ingredient.

$R^1$ represents —$CO_2R^5$ or —$CONR^6R^7$. Here, $R^5$ represents a hydrogen atom, or a straight or branched alkyl group having 1 to 12 carbon atoms, or an aralkyl group having 7 to 12 carbon atoms, or a cycloalkyl group having 4 to 7 carbon atoms which may be unsubstituted or substituted by at least one alkyl group having 1 to 4 carbon atoms, or a substituted or unsubstituted phenyl group, or a monoequivalent cation. As the straight or branched alkyl group having 1 to 12 carbon atoms, there may be mentioned, for example, methyl, ethyl, n-propyl, iso-propyl, n-butyl, sec-butyl, tert-butyl, n-pentyl, iso-amyl, n-hexyl, n-heptyl, n-octyl, n-nonyl, n-decyl, n-undecyl, n-dodecyl, etc.

As the aralkyl group having 7 to 12 carbon atoms, there may be mentioned, for example, benzyl, 1-phenethyl, 2-phenethyl, 3-phenylbutyl, 4-phenylbutyl, 1-(2-naphthyl)ethyl, 2-(1-naphthyl)ethyl, etc.

As the cycloalkyl group having 4 to 7 carbon atoms which is unsubstituted or substituted by at least one of an alkyl group having 1 to 4 carbon atoms, there may be mentioned, for example, cyclobutyl, 1-propylcyclobutyl, 1-butylcyclobutyl, 2-methylcyclobutyl, 2-propylcyclobutyl, 3-ethylcyclobutyl, 3-propylcyclobutyl, 2,3,4-triethylcyclobutyl, cyclopentyl, 3-ethylcyclopentyl, 3-propylcyclopentyl, 3-butylcyclopentyl, 3-tert-butylcyclopentyl, 2,2-dimethylcyclopentyl, (1-methyl-3-propyl)cyclopentyl, (2-methyl-4-propyl)cyclopentyl, cyclohexyl, 3-ethylcyclohexyl, 3-iso-propylcyclohexyl, 4-methylcyclohexyl, 4-ethylcyclohexyl, 4-propylcyclohexyl, 4-tert-butylcyclohexyl, 2,2-dimethylcyclohexyl, 2,6-dimethylcyclohexyl, (2,6-dimethyl-4-propyl)cyclohexyl, cycloheptyl, etc. As the substituent of the substituted or unsubstituted phenyl group, there may be preferred, for example, a halogen atom, a hydroxy group, an acyloxy group having 2 to 7 carbon atoms, an alkyl group having 1 to 4 carbon atoms which may be substituted by a halogen atom, an alkoxy group having 1 to 4 carbon atoms which may be substituted by a halogen atom, a nitrile group, a carboxy group or an alkoxycarbonyl group having 2 to 7 carbon atoms, etc. Here, as the halogen atom, there may include fluorine, chlorine or bromine, etc., and particularly, fluorine or chlorine is preferred. As the acyloxy group having 2 to 7 carbon atoms, there may be mentioned, for example, acetoxy, propionyloxy, n-butyryloxy, iso-butyryloxy, n-valeryloxy, iso-valeryloxy, caproyloxy, enantyloxy or benzoyloxy, etc.

As the alkyl group having 1 to 4 carbon atoms which may be substituted by halogen, there may be mentioned such as methyl, ethyl, n-propyl, iso-propyl, n-butyl, chloromethyl, dichloromethyl, trifluoromethyl, etc., as preferred ones. As the alkoxy group having 1 to 4 carbon atoms which may be substituted by halogen, there may be mentioned methoxy, ethoxy, n-propoxy, iso-propoxy, n-butoxy, chloromethoxy, dichloromethoxy, trifluoromethoxy, etc., as preferred ones. As the alkoxycarbonyl group having 2 to 7 carbon atoms, there may be mentioned methoxycarbonyl, ethoxycarbonyl, butoxycarbonyl, hexyloxycarbonyl, etc. As the number of the substituents, they may have 1 to 3 substituents as mentioned above, preferably 1. As the monoequivalent cation, there may be mentioned, for example, alkali metal cations such as $Na^+$, $K^+$, etc., divalent or trivalent metal cations such as $\kappa Ca^{2+}$, $\kappa Mg^{2+}$, $\frac{1}{3}Al^{3+}$, etc., ammonium cations such as an ammonium ion, a tetramethylammonium ion, etc.

$R^6$ and $R^7$ in the —$CONR^6R^7$ group may be the same or different, each represents a hydrogen atom, or an alkyl group having 1 to 10 carbon atoms, or $R^6$ and $R^7$ may be combined with a nitrogen atom which is bonded to them to form a substituted or unsubstituted 5 -to 6-membered ring which may have further hetero atoms. Here, as the alkyl group having 1 to 10 carbon atoms, there may be mentioned, for example, methyl, ethyl, n-propyl, iso-propyl, n-butyl, sec-butyl, tert-butyl, n-pentyl, iso-amyl, n-hexyl, n-heptyl, n-octyl, n-nonyl, n-decyl, etc.

Also, as the substituents for the above-mentioned substituted or unsubstituted ring, an alkyl group having 1 to 4 carbon atoms which may be substituted by a halogen atom is preferred and there may be mentioned, for example, methyl, ethyl, n-propyl, iso-propyl, n-butyl, chloromethyl, dichloromethyl, trifluoromethyl, etc. The above substituted or unsubstituted ring may have the above substituents with 1 to 3, preferably 1. Also, as the hetero atom, there may be mentioned a nitrogen, a sulfur or an oxygen atom. As the above ring, there may be mentioned, for example, 1-pyrrolidyl, thiazolyl, 1-piperidyl, morpholyl, piperazyl or 5,6-dihydrophenanthridyl group, etc.

As $R^1$, there may be mentioned —$COOR^5$ where $R^5$ is a straight or branched alkyl group having 1 to 12 carbon atoms, and particularly a carboxyl group, a methoxycarbonyl group or an ethoxycarbonyl group is preferred.

A is
(i) —CH═CH—CH$_2$CH$_2$— or
(ii) —CH$_2$CH$_2$—O—CH$_2$—;
and B represents —C≡C— group.

R$^2$ represents a straight or branched alkyl group having 3 to 10 carbon atoms, or a cycloalkyl group having 4 to 7 carbon atoms which may be unsubstituted or substituted by at least one alkyl group having 1 to 4 carbon atoms, or a straight or branched alkenyl group having 3 to 12 carbon atoms, or a straight or branched alkynyl group having 3 to 8 carbon atoms, or a substituted alkyl group having 1 to 3 carbon atoms which is substituted by a phenyl group or a phenoxy group which may be substituted, or an alkoxy group having 1-6 carbon atoms, or a cycloalkyl group having 5 to 8 carbon atoms. Here, as the straight or branched alkyl group having 3 to 10 carbon atoms, there may be mentioned n-propyl, n-butyl, n-pentyl, 1-methylpentyl, 2-methylpentyl, 1,2-dimethylpentyl, n-hexyl, 1-methylhexyl, 2-methylhexyl, 1,2-dimethylhexyl, n-heptyl, n-octyl, n-nonyl, n-decyl, etc., preferably n-pentyl, 1-methylpentyl, 2-methylpentyl, 1,2-dimethylpentyl, n-hexyl, 1-methylhexyl, 2-methylhexyl, etc.

As the cycloalkyl group having 4 to 7 carbon atoms which is unsubstituted or substituted by at least one alkyl group having 1 to 4 carbon atoms, there may be mentioned cyclobutyl, 1-propylcyclobutyl, 1-butylcyclobutyl, 1-pentylcyclobutyl, 2-methylcyclobutyl, 2-propylcyclobutyl, 3-ethylcyclobutyl, 3-propylcyclobutyl, 2,3,4-triethylcyclobutyl, cyclopentyl, 2-pentylcyclopentyl, 2,2-dimethylcyclopentyl, 3-ethylcyclopentyl, 3-propylcyclopentyl, 3-butylcyclopentyl, 3-tert-butylcyclopentyl, (1-methyl-3-propyl)cyclopentyl, (2-methyl-3-propyl)cyclopentyl, (2-methyl-4-propyl)cyclopentyl, cyclohexyl, 3-ethylcyclohexyl, 3-iso-propylcyclohexyl, 4-methylcyclohexyl, 4-ethylcyclohexyl, 4-propylcyclohexyl, 4-tert-butylcyclohexyl, 2,6-dimethylcyclohexyl, 2,2-dimethylcyclohexyl, (2,6-dimethyl-4-propyl)cyclohexyl, cycloheptyl, etc., preferably cyclopentyl, cyclohexyl, etc.

As the straight or branched alkenyl group having 3 to 12 carbon atoms, there may be mentioned, for example, allyl, 3-butenyl, 2-butenyl, 3-methyl-2-butenyl, 4-pentenyl, 4-methyl-3-pentenyl, 2-pentenyl, 5-hexenyl, 4-hexenyl, 3-methyl-4-hexenyl, 5-methyl-2-hexenyl, 2,5-dimethyl-3-hexenyl, 6-heptenyl, 5-heptenyl, 2-ethyl-5-hepteny, 2,6-dimethyl-5-heptenyl, 7-octenyl, 8-nonenyl, 9-decenyl, 10-undecenyl, 11-dodecenyl, etc., preferably 3-pentenyl, 2,6-dimethyl-5-heptenyl, etc.

As the straight or branched alkynyl group having 3 to 8 carbon atoms, there may be mentioned propargyl, 2-butynyl, 3-butynyl, 2-methyl-3-butynyl, 2-ethyl-3-butynyl, 4-pentynyl, 3-pentynyl, 1-ethyl-3-pentynyl, 1-methyl-3-pentynyl, 2-methyl-3-pentynyl, 1,2-dimethyl-3-pentynyl, 1,1-dimethyl-3-pentynyl, 2,2-dimethyl-3-pentynyl, 3-hexynyl, 1-methyl-3-hexynyl, 2-methyl-3-hexynyl, 1,2-dimethyl-3-hexynyl, 1,1-dimethyl-3-hexynyl, 2,2-dimethyl-3-hexynyl, 4-heptynyl, 5-octynyl, etc., preferably 1-methyl-3-pentynyl, 1-methyl-3-hexynyl, 2-methyl-3-hexynyl, etc.

As the alkyl group of the substituted alkyl group having 1 to 3 carbon atoms which is substituted, they may be either straight or branched, and may be mentioned, for example, methyl, ethyl, n-propyl and isopropyl. These alkyl groups may be substituted by a phenyl group; a phenoxy group, an alkoxy group having 1 to 6 carbon atoms such as methoxy, ethoxy, n-propoxy, n-butoxy, iso-butoxy, tert-butoxy, n-pentoxy, n-hexoxy, etc.; or a cycloalkyl group having 5 to 8 carbon atoms such as cyclopentyl, cyclohexyl, etc. These substitutents may further be substituted by the substituents mentioned as substituents for R$^5$. As the substituted alkyl group having 1 to 3 carbon atoms, of these, preferred are, for example, an alkyl group having 1 to 2 carbon atoms substituted by a phenoxy group or a phenyl group which may be substituted by a fluorine atom, a chlorine atom, methyl, ethyl or a trifluoromethyl group, or propoxymethyl, 2-ethoxyethyl, 2-propoxyethyl, butoxymethyl, (2-ethoxy-1-methyl)ethyl, cyclohexylmethyl, 1-cyclohexylethyl, 2-cyclohexylethyl, etc.

As R$^2$, particularly n-pentyl, 2-methylpentyl, 1,1-dimethylpentyl, 1-methylhexyl, 2-methylhexyl, 2,6-dimethyl-5-heptenyl, 1-methyl-3-pentynyl, 1-methyl-3-hexynyl, 2-methyle-3-hexynyl, (2-ethoxy-1-methyl)ethyl, cyclopentyl, cyclohexyl, 2-cyclohexylethyl, 1-cyclohexylethyl, phenethyl are preferred.

As R$^3$, there may be mentioned a hydrogen atom, methyl or vinyl group.

R$^4$ represents a hydrogen atom, an acyl group having 1 to 7 carbon atoms, a tri(1 to 7 carbon atoms)hydrocarbylsilyl group, or a group forming an acetal bond with an oxygen atom of a hydroxy group. Here, as the acyl group having 1 to 7 carbon atoms, there may be mentioned, for example, acetyl, propionyl, n-butyryl, iso-butyryl, n-valeryl, iso-valeryl, caproyl, enanthyl, benzoyl, etc., preferably acetyl or benzoyl, etc.

As the tri(1 to 7 carbon atoms)hydrocarbyl-silyl group, there may be mentioned, for example, tri(1 to 4 carbon atoms)alkylsilyl such as trimethylsilyl, triethylsilyl and tert-butyldimethylsilyl groups; diphenylalkylsilyl such as tert-butyldiphenylsilyl group; tribenzylsilyl group; dimethyl(2,4,6-tri-tert-butylphenoxy)silyl group, etc., as preferred ones.

As the group which forms an acetal bond with an oxygen atom of a hydroxy group, there may be mentioned, for example, methoxymethyl, 1-ethoxyethyl, 2-methoxypropyl, 2-ethoxy-2-propyl, (2-methoxyethoxy)methyl, benzyloxymethyl, 2-tetrahydropyranyl, 2-tetrahydrofuranyl, 4-(4-methoxytetrahydropyranyl) groups or a 6,6-dimethyl-3-oxa-2-oxobicyclo[3,1,0]hex-4-yl group.

Among these, 2-tetrahydropyranyl, 2-tetrahydrofuranyl, 1-ethoxyethyl, 2-methoxy-2-propyl, (2-methoxyethoxy)methyl, 4-(4-methoxytetrahydropyranyl), 6,6-dimethyl-3-oxa-2-oxobicyclo[3,1,0]hex-4-yl groups are preferred.

As R$^4$, of these, a hydrogen atom, a tert-butyldimethylsilyl group, a tert-butylphenylsilyl group, a 2-tetrahydropyranyl group, an acetyl group, a 4-(4-methoxytetrahydropyranyl) group, a 6,6-dimethyl-3-oxa-2-oxobicyclo[3,1,0]hex-4-yl group and a dimethyl(2,4,6-tritert-butylphenoxy)silyl group are particularly preferred.

Specific examples of the prostacyclins to be provided by the present invention are enumerated below.
(1) 4,5,13,14-tetradehydro-9(0)-methano-$\Delta^{6(9\alpha)}$-prostaglandin I$_1$
(2) 4,5,13,14,18,18,19,19-octadehydro-16-methyl-9(0)-methano-$\Delta^{6(9\alpha)}$-prostaglandin I$_1$
(3) 4,5,13,14,18,18,19,19-octadehydro-16,20-dimethyl-9(0)-methano-$\Delta^{6(9\alpha)}$-prostaglandin I$_1$ (4) 4,5,13,14,18,18,19,19-octahydro-17,20-dimethyl-9(0)-methano-$\Delta^{6(9\alpha)}$-prostaglandin $I_1$
(5) 4,5,13,14-tetradehydro-16,17,18,19,20-pentanor-15-cyclopentyl-9(0)-methano-$\Delta^{6(9\alpha)}$-prostaglandin $I_1$
(6) 4,5,13,14-tetradehydro-16,17,18,19,20-pentanor-15-cyclohexyl-9(0)-methano-$\Delta^{6(9\alpha)}$-prostaglandin $I_1$
(7) 3-oxa-13,14-didehydro-16,17,18,19,20-pentanor-15-cyclopentyl-9(0)-methano-$\Delta^{6(9\alpha)}$-prostaglandin $I_1$
(8) 3-oxa-13,14-didehydro-16,17,18,19,20-pentanor-15-cyclohexyl-9(0)-methano-$\Delta^{6(9\alpha)}$-prostaglandin $I_1$
(9) 3-oxa-13,14,18,18,19,19-hexadehydro-16-methyl-9(0)-methano-$\Delta^{6(9\alpha)}$-prostaglandin $I_1$
(10) 3-oxa-13,14,18,18,19,19-hexadehydro-16,20-dimethyl-9(0)-methano-$\Delta^{6(9\alpha)}$-prostaglandin $I_1$
(11) 3-oxa-13,14,18,18,19,19-hexadehydro-16,20-dimethyl-9(0)-methano-$\Delta^{6(9\alpha)}$-prostaglandin $I_1$
(12) methyl ester of (1) to (11)
(13) ethyl ester of (1) to (11)
(14) tert-butyl ester of (1) to (11)
(15) 11-tert-butyldimethylsilyl ether of (12)
(16) 11-tert-butyldimethylsilyl ether of (13)
(17) 11-tert-butyldimethylsilyl ether of (14)
(18) 15-tert-butyldimethylsilyl ether of (15)
(19) 15-tert-butyldimethylsilyl ether of (16)
(20) 15-tert-butyldimethylsilyl ether of (17)
(21) 11-(tetrahydro-2-pyranyl) ether of (12)
(22) 11-(tetrahydro-2-pyranyl) ether of (13)
(23) 11-(tetrahydro-2-pyranyl) ether of (14)
(24) 15-(tetrahydro-2-pyranyl) ether of (21)
(25) 15-(tetrahydro-2-pyranyl) ether of (22)
(26) 15-(tetrahydro-2-pyranyl) ether of (23)
(27) sodium salt, ammonium salt or potassium salt of carboxylic acid of (1) to (11)

(PHARMACEUTICAL)

In application of the compounds of the present invention for clinical uses as the blood flow ameliorator, antithrombotic, antihypertensive and antiulcer, the effective administration method may be either oral or parenteral, and it is desired to be administered at a dose of 0.1 μg to 100 mg per one administration, preferably at a daily dose of 1 μg to 1 mg in one or several divided doses. However, the accurate dosage depends on the age, body weight, severity of disease of the patient, the administration route and the number of administrations.

The solid preparations for oral administration may include tablets, pills, powders, and granules. In such solid preparations, one or more active substances may be mixed with at least one inert diluent including, for example, half-digestable starch, potato starch, alginic acid, mannitol or lactose.

The preparation may also contain additives other than diluents, for example, lubricants such as magnesium stearate, according to a conventional manner. The liquid preparations for oral administration may contain parmaceutically acceptable emulsifiers, solutions, suspensions or elexirs, and may also contain, in addition to inert diluents employed in general, auxiliary agents, for example, wetting agents, suspension aids, sweetners, flavors, aromatics or preservatives. As other preparations for oral administration, there may also be included capsules of absorbable materials such as gelatin containing one or more active substance together with or without diluents or excipients.

As the solid preparation for rectal administration, there may included suppositories comprising at least one inert base containing one or more active substance, for example, cacao butter, macrogol, Witepsol, and which can be treated according to the method known per se. Further, as the preparation for topical application, ointments, etc. may be mentioned.

The product for parenteral administration contains sterile aqueous or non-aqueous solvents, or emulsifiers. Non-aqueous solvents or suspending agents may include propylene glycol, polyethylene glycol, vegetable oils such as olive oil and injectable organic acid esters such as ethyl oleate. Such preparations can also contain auxiliary agents such as preservatives, wetting agents, emulsifiers and dispersants. They can be sterilized by, for example, filtration through a bacteria retaining filter, formulation with a sterilizer or by irradiation. It is also possible to prepare sterile solid preparations to be used by dissolving them in a sterile solvent for injection immediately before use.

(SYNTHETIC METHOD)

The compound of the present invention represented by the formula (I) can be produced according to, for example, the route shown below by use of the known compound (VI) as a starting material as disclosed together with its synthetic method in [Collected Gists of Lectures, pp. 51 to 54, the 45th Symposium on the synthetic organic chemistry (sponsored by The Society of Synthetic Organic Chemistry)].

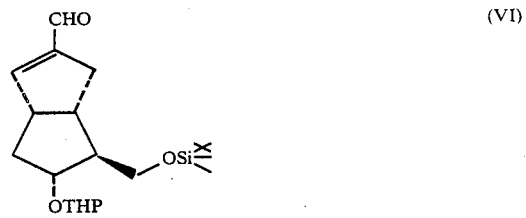

[wherein

represents a t-butyldimethylsilyl group and THP represents a tetrahydro-2-pyranyl group.)]

In the formula [I], the compound where A is —CH=CH—CH$_2$CH$_2$—, B is —C≡C— and $R^3$ is a hydrogen can be prepared by the synthetic route shown in Route 1.

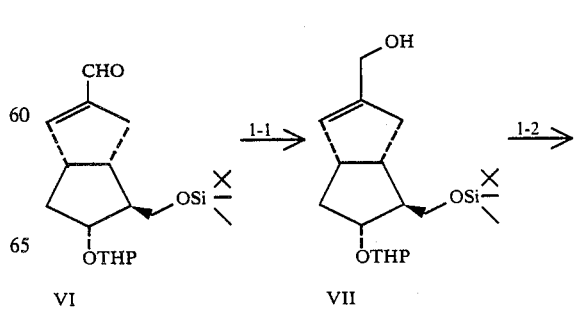

-continued

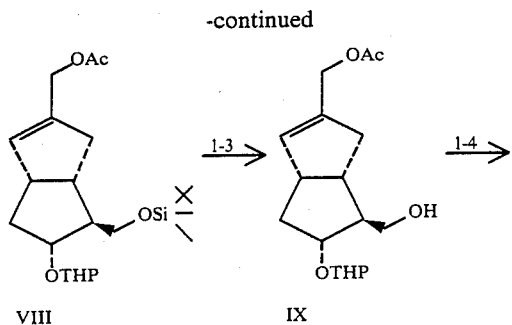

VIII → 1-3 → IX → 1-4 →

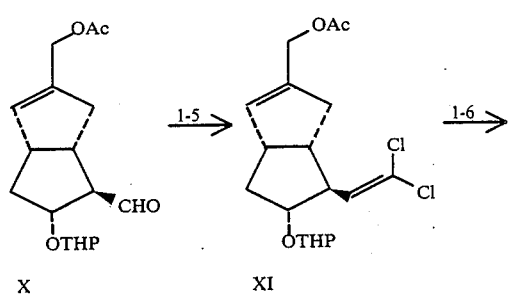

X → 1-5 → XI → 1-6 →

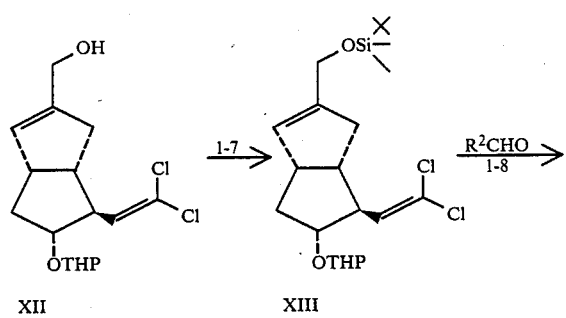

XII → 1-7 → XIII → R²CHO / 1-8 →

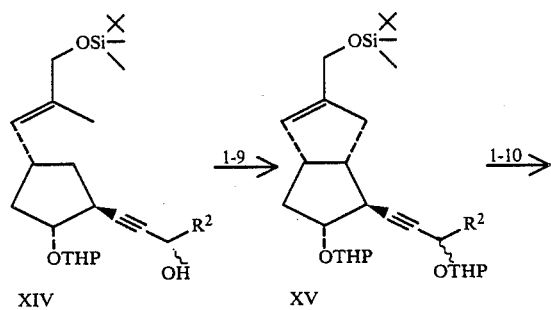

XIV → 1-9 → XV → 1-10 →

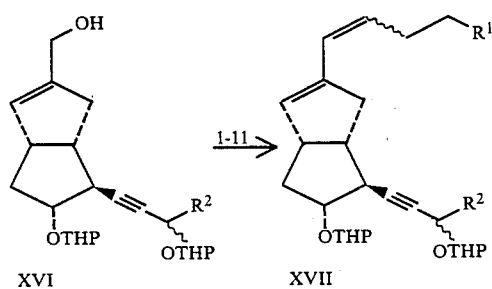

XVI → 1-11 → XVII

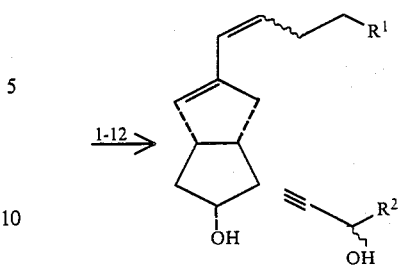

XVIII 1-12 →

[wherein THP,

$R^1$ and $R^2$ are the same as defined above. Ac represents an acetyl group.]

ROUTE 1

Step 1-1 can easily be accomplished by reducing the compound (VI) by sodium borohydride, diisobutylaluminum hydride or the like. The reaction may be carried out in an alcohol such as methanol, ethanol, etc. or in toluene at −78° C. to 0° C.

Step 1-2 is a step in which the compound (VII) is acetylized with acetyl chloride or acetic anhydride. The reac-tion may be carried out in pyridine or in dichloromethane in the presence of triethylamine at a reaction temperature of −70° C. to 50° C., preferably −20° C. to 30° C.

Step 1-3 is a step to in which the compound (VIII) is desilylated with fluorine compounds such as tetra-n-butylammonium fluoride or cesium fluoride, etc. The reaction is generally carried out in ethers such as tetrahydrofuran, ethyl ether, etc. at 0° C. to 30° C.

Step 1-4 is a step in which the compound (IX) is oxidized to convert it to the compound (X). For oxidation reaction, the oxidizing method using the system of triethylamine-sulfur trioxide!pyridine complex-dimethylsulfoxide is particularly preferably employed. A reaction temperature is generally 10° to 40° C. and an amount of the oxidizing agent employed may preferably be in an excess, namely 2 to 100-fold moles.

Step 1-5 is a step in which a base-treated $$\underset{O}{\overset{\parallel}{EtO_2PCl_3}}$$

is allowed to react with the compound [X] to obtain the compound [X]. As the base, n-butyllithium is particularly preferred. The reaction is carried out in tetrahydrofuran, ethyl ether or a mixed solvent of tetrahydrofuran-ethyl ether and a reaction temperature may be −100° C. to 50° C., particularly preferred is starting the reaction at −100° C. and then gradually elevating the temperature upto room temperature.

Step 1-6 is a step to effect deacetylation by treating the compound (XI) with potassium carbonate in an alcohol such as methanol, ethanol and the like. A reaction temperature may be −70° C. to 50° C., and preferably it may be carried out at −20° C. to 30° C.

Step 1-7 is a step in which the compound (XII) is treated with t-butyldimethylsilyl chloride in dimethylformamide in the presence of imidazole to obtain the compound (XIII). The reaction may be carried out at −50° C. to 50° C., preferably 0° C. to 30° C.

Step 1-8 is a step in which, after treatment of the compound (XIII) with a base, an aldehyde R²CHO is allowed to react to obtain the compound (XIV). As the base, n-butyllithium is particularly preferred, and the reaction may be carried out in ethers such as ether, tetrahydrofuran, etc. at −100° C. to 50° C., preferably −78° C. to 30° C.

Step 1-9 is a step in which dihydropyran is allowed to react to the compound (XIV) in the presence of an acid catalyst to obtain the compound (XV). As the acid catalyst, p-toluenesulfonic acid, phosphor oxychloride, etc. may be used and the reaction is carried out in dichloromethane at −70° C. to 50° C., preferably −20° C. to 30° C.

Step 1-10 is a step in which the compound (XV) is desilylated in accordance with the same reaction procedure in Step 1-3. Step 1-11 is a step in which the hydroxymethyl group in the compound (XVI) is oxidized to convert it to a formyl group in the same reaction procedure as in Step 1-4, and then allowing it to react with the Wittig reagent Ph₃P=CHCH₂CH₂R¹ to obtain the compound (XVII). The Wittig reagent may be formed by treating a base to Ph₃R⁺CH₂CH₂CH₂RX⁻ in the reaction system (where X represents chlorine, bromine or iodine).

As the base employed, sodium amide, sodium hydride, potassium hydride, potassium t-butoxide, n-butyllithium, etc. are preferred. The reaction may be carried out in a solvent such as dimethylsulfoxide, dimethylformamide, ethyl ether, tetrahydrofuran, dimethoxyethane, toluene, etc., at −100° C. to 100° C., preferably −100° C. to 30° C.

Step 1-12 is a step in which by treating the compound (XVII) is treated under an acidic condition to obtain the compound (XVIII). The reaction may be carried out in an mixed solvent of acetic acid-water-tetrahydrofuran at −10° C. to 80° C., preferably 5° C. to 60° C.

In the formula [I], the compound where A is —CH₂CH₂—O—CH₂—, B is —C≡C— and R³ is hydrogen can be prepared by the synthetic route shown in Route 2.

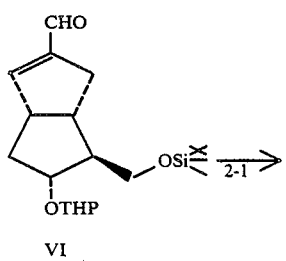

VI

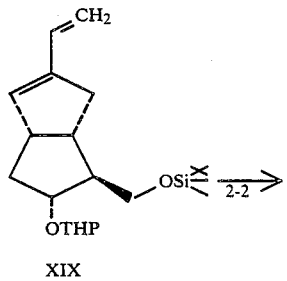

XIX

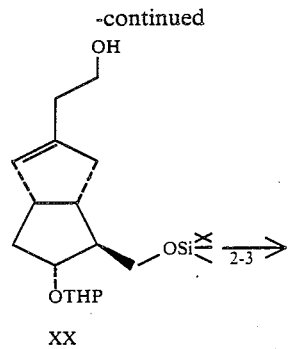

XX

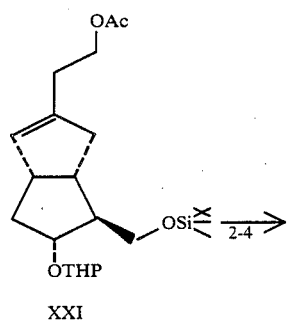

XXI

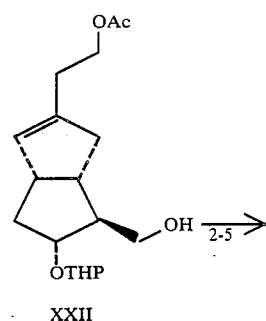

XXII

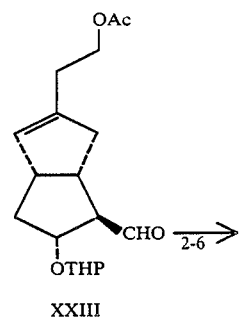

XXIII

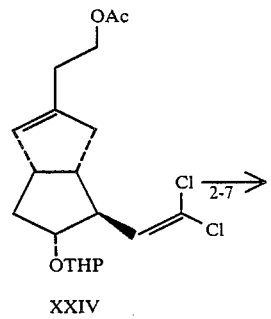

XXIV

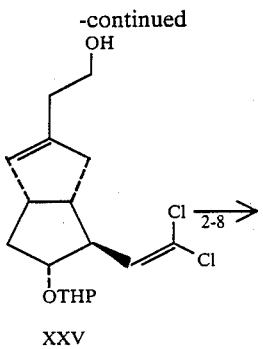

XXV

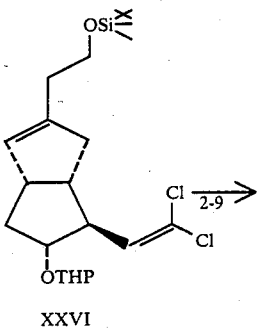

XXVI

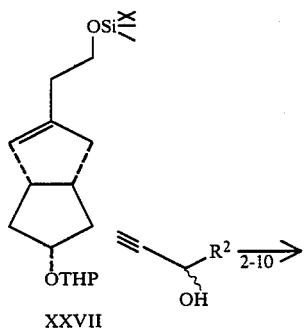

XXVII

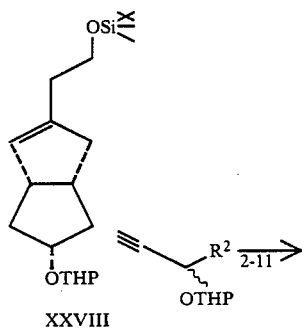

XXVIII

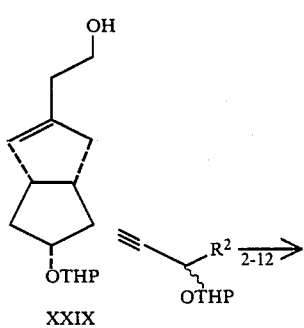

XXIX

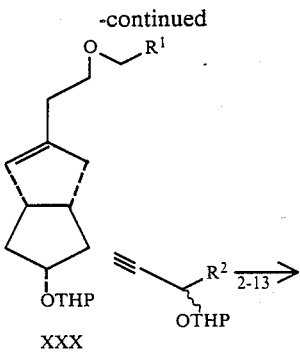

XXX

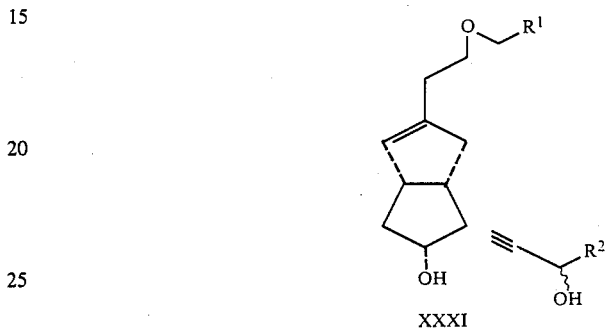

XXXI

[wherein THP,

Si≤, $R^1$, $R^2$ and Ac are the same meanings as defined above.]

ROUTE 2

Step 2-1 is a step in which the compound [VI] is allowed to react with the Wittig reagent, etc. to obtain the compound [XIX]. As the Wittig reagent, a Wittig reagent obtained by reacting a base such as sodium hydride or potassium tert-butoxide to methyltriphenylphosphonium bromide is preferred. The reaction may be carried out in ethers such as ethyl ether, tetrahydrofuran, etc., or in dimethylsulfoxide, at generally 0° C. to 40° C. Step 2-2 is a step in which the compound [XIX] is allowed to selective hydroboration, and then oxidized it under an alkaline condition to obtain the compound [XX]. As the selective hydroboration agent, stereoscopically bulky reagent is preferred and disiamylborane is particularly preferred. The reaction may be carried out in ethers such as tetrahydrofuran, ethyl ether, etc. at generally −30° C. to 0° C., and then oxidation is carried out under an alkaline condition. Particularly preferably, the oxidation reaction may be carried out by use of 6N-aqueous caustic soda solution and 30% aqueous hydrogen peroxide solution at 0° C. to 30° C. Step 2-3 is a step in which the compound [XXI] is obtained from the compound [XX] by entirely the same reaction procedure as Step 1-2. Step 2-4 to Step 2-11 can be carried out in the same reaction procedure as in Step 1-3 to Step 1-10. Step 2-12 is a step in which the compound [XXIX] is allowed to react with $XCH_2R^1$ (where X is a halogen atom. $R^1$ is the same as defined above.) in the presence of a base and optionally the presence of a catalyst to obtain the compound [XXX]. As the base, sodium hydride, potassium tert-butoxide, potassium hydroxide, sodium hydroxide, etc. may be employed. The reaction may be carried out in an aromatic hydrocarbon such as benzene, toluene, etc.; ethers such as tetrahydrofuran, ethyl ether, etc.; halogenated hydrocarbon such as dichloromethane, chloroform, etc.; or in dimethylformamide, dimethylsulfoxide, etc. at −50° C. to 150° C., preferably 0° C. to 100° C. When the aromatic hydrocarbon, ethers, halogenated hydrocarbon or the like is employed as the reaction solvent, it may be carried out as the bilayer reaction with water in the presence of a phase transfer catalyst such as tetrabutylammonium bisulfate ($Bu_4N^+HSO_4^\times$). Step 2-13 can be carried out in the same reaction procedure as in Step 1-12.

In the formula [I], the compound where $R^1$ is COOH can be prepared by the synthetic route as shown in Route 3.

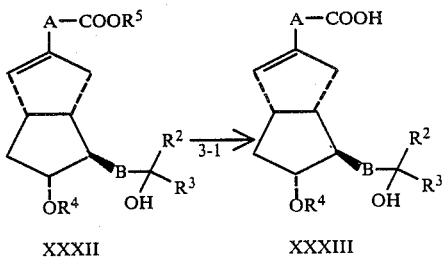

XXXII          XXXIII

[wherein A, B, $R^2$, $R^3$, $R^4$ and $R^5$ are the same as defined above.]

ROUTE 3

Hydrolysis reaction of Step 3-1 may be carried out in a single or mixed solvent of water, methanol or ethanol containing sodium hydroxide or potassium oxide at −10° C. to 100° C., or carried out, for example, by using an enzyme such as lipase, etc. in water or a solution containing water at −10° C. to 60° C. The formed compound [XXXIII] is allowed to salt forming reaction, if necessary, to provide a corresponding carboxylic acid salt. The salt forming reaction itself has been known and can be carried out by neutralizing reaction in the usual manner with approximately equivalent amount of a basic compound such as potassium hydroxide, sodium hydroxide, etc., or ammonia, trimethylamine, monoethanolamine or morpholine with that of carboxylic acid.

In the formula [I], the compound where $R^4$ is a hydrogen atom can be prepared by the synthetic route as shown in Route 4.

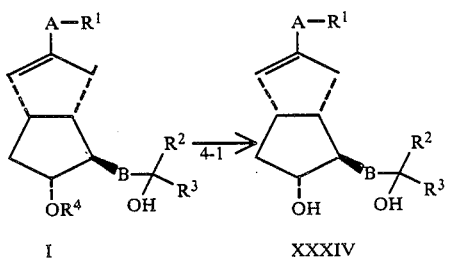

I          XXXIV

[wherein A, B, $R^1$, $R^2$ and $R^3$ are the same as defined above, and $R^4$ is the substituent as defined above except for a hydrogen atom.]

ROUTE 4

Step 4-1 is an elimination step of a protective group for a hydroxyl group. Elimination of the protective group for a hydroxyl group may be carried out, when the protective group is a group forming an acetal bond with an oxygen atom of the hydroxy group, for example, by using am acetic acid, a pyridinium salt of p-toluenesulfonic acid or a cation exchange resin as a catalyst and, for example, using water, tetrahydrofuran, dioxane or the like as the solvent at −78° C. to 80° C.

Also, when the protective group is a tri(1 to 7 carbon atoms)hydrocarbylsilyl group, for example, it may be carried out in the presence of acetic acid, tetranbutylammonium fluoride, cesium fluoride, etc. in the aforesaid solvent at −78° C. to 80° C. Also, when the protective group is an acyl group, it may be carried out, for example, in the aqueous solution of potassium hydroxide, sodium hydroxide or calcium hydroxide; or water-alcohol mixed soluiton; or in the solution of methanol, ethanol, etc. containing potassium carbonate, sodium carbonate, sodium methoxide, potassium methoxide, sodium ethoxide or the like.

[BEST EMBODIMENT FOR CARRYING OUT THE INVENTION]

In the following, the present invention will be explained by referring to Examples, but it is not limited by these.

REFERENCE EXAMPLE 1

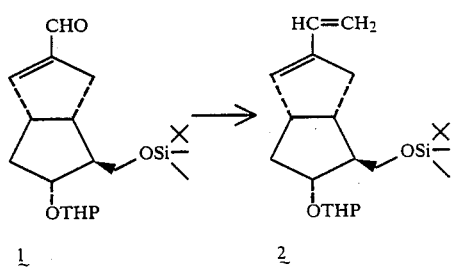

1          2

In anhydrous THF (5 ml) was dissolved methyltriphenylphosphonium bromide (357 mg, 1 mmol) and potassium tert-butoxide (116 mg, 1 mmol) in anhydrous THF (5 ml) solution was added thereto at room temperature. Then, α, β-unsaturated aldehyde 1 (190 mg, 0.5 mmol) in anhydrous THF (5 ml) solution was added thereto and the mixture was stirred at room temperature for 30 minutes. After completion of the reaction, a saturated aqueous NH₄Cl solution was added thereto and the mixture was extracted with ethyl ether. The extract was washed with a saturated saline solution, dried over anhydrous magnesium sulfate and then the solvent was evaporated under reduced pressure. The resulting residue was passed through silica gel column chromatography to obtain a diene derivative 2 (171 mg, 90.5%) as colorless oily product.

IR (neat): 2940, 1638, 1597 cm$^{-1}$.

NMR δ (CDCl₃): 6.52 (dd, J=16, 10Hz, 1H), 5.63 (bs, 1H), 5.00 (m, 2H), 4.62 (m, 1H), 3.00 (m, 1H), 0.90 (s, 9H), 0.05 (s, 6H).

Mass m/z: 294 [M$^+$-84], 277, 237, 85.

REFERENCE EXAMPLE 2

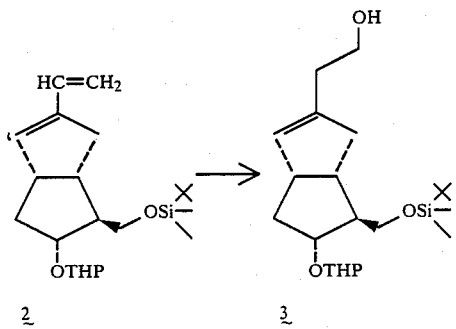

Under argon atmosphere, the diene derivative 2 (100 mg, 0.266 mmol) was dissolved in THF (1.5 ml) and disiamylborane-THF solution (0.59 M, 0.9 ml) was added thereto at −10° C. After stirring for 3 hours, disiamylborane-THF solution (0.59 M, 0.45 ml) was further added thereto and stirred for 1.5 hours. Then, a 6N-NaOH aqueous solution (0.27 ml) and a 30% aqueous hydrogen peroxide solution (0.2 ml) were added thereto and the mixture was stirred at room temperature for 1.5 hours. Subsequently, the reaction mixture was extracted with ether and the extract was washed with a saturated aqueous sodium thiosulfate solution and a saturated saline solution. The extract was dried over anhydrous magnesium sulfate, the solvent was evaporated and the residue was purified through silica gel column chromatography to obtain homoallyl alcohol 3 (97 mg, 92.6%) as colorless oily product.

IR (neat): 3400, 2925, 1470, 1255 cm$^{-1}$.
NMR δ (CDCl$_3$): 5.43 (bs, 1H), 4.60 (m, 1H), 3.00 (m, 1H), 0.92 (s, 9H), 0.05 (s, 6H).
Mass m/z: 312 [M$^+$-84], 255, 237.

REFERENCE EXAMPLE 3

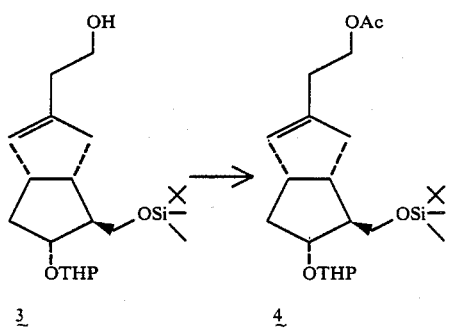

Under argon atmosphere, homoallyl alcohol 3 (1.0 g, 2.57 mmol) was dissolved in 5 ml of pyridine, anhydrous acetic acid (0.32 ml, 3.34 mmol) was added thereto under ice-cooling and the mixture was stirred at room temperature for 3 hours. The reaction mixture was poured into a saturated aqueous NaHCO$_3$ solution and extracted with ethyl ether. Pyridine was removed by using a 10 % copper sulfate, and the extract was washed with water and dried over anhydrous magnesium sulfate. After evaporation of the solvent, the resulting residue was passed through silica gel column chromatography to obtain an acetate derivative 4 (1.042 g, 92.5%) as colorless oily product.

IR (neat): 2935, 1740, 1240 cm$^{-1}$.

REFERENCE EXAMPLE 4

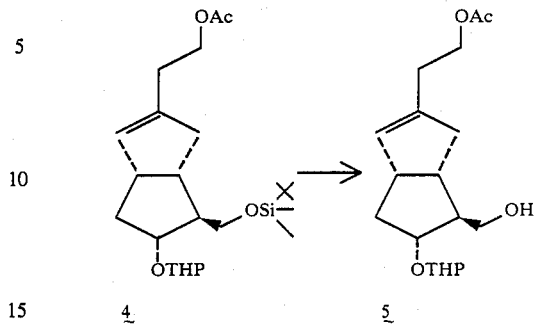

Under argon atmosphere, the acetate derivative 4 (1.04 g, 2.38 mmol) was dissolved in 20 ml of THF and tetrabutylammonium fluoride (3.6 ml, 3.6 mmol) was added thereto at −10° C., and the mixture was stirred at room temperature for 2 hours and 30 minutes. A saturated aqueous NH$_4$Cl solution was added thereto and the mixture was extracted with ethyl ether, washed with a saturated aqueous NaHCO$_3$ solution and a saturated saline solution and then dried over anhydrous magnesium sulfate. After evaporation of the solvent, the obtained residue was passed through silica gel column chromatography to obtain an alcohol derivative 5 (632 mg, 75.9 %).

IR (neat): 3450, 2950, 1735, 1240 cm$^{-1}$.

REFERENCE EXAMPLE 5

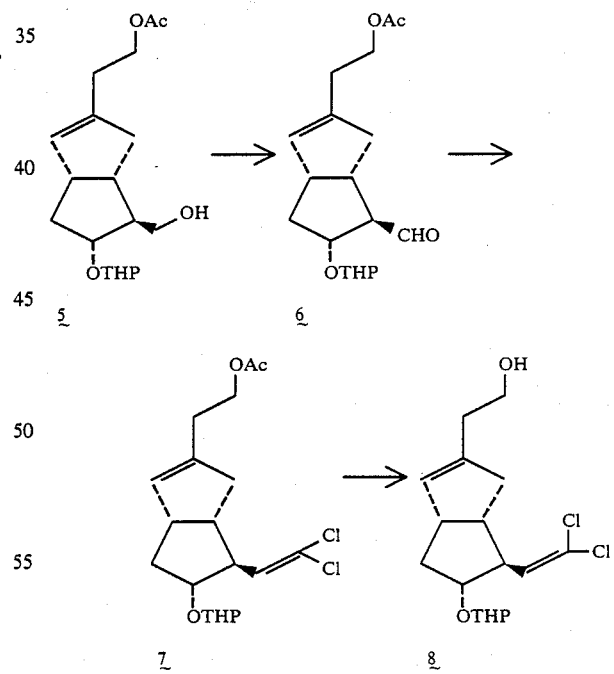

Under argon gas atmosphere, the alcohol derivative 5 (632 mg, 1.95 mmol) was dissolved in a mixed solvent of 1.6 ml of dimethylsulfoxide and 3.1 ml of triethylamine, and a solution of SO$_3$-pyridine complex (3.65 g, 23 mmol) dissolved in 4.7 ml of DMSO was added thereto under room temperature and stirred for 10 minutes. The mixture was poured into ice-cold water, extracted with ethyl ether, washed with water and then dried over anhydrous magnesium sulfate, and then the solvent was evaporated to obtain an aldehyde derivative 6. Under argon atmosphere, ethyl trichloromethylphosphonate (1.07 g, 4.17 mmol) was dissolved in a mixed solvent of 16.7 ml of ethyl ether and 11 ml of THF and the mixture was cooled to −100° C. n-Butyllithium (2.7 ml, 4.17 mmol) was added thereto and the mixture was stirred for 40 minutes, subsequently the above ethyl ether solution of the aldehyde derivative 6 was added thereto. The temperature was gradually raised up to 0° C., and after 30 minutes, a saturated NH₄Cl solution was added thereto and the reaction mixture was extracted with ehtyl ether and washed with water. After drying over anhydrous magnesium sulfate, the solvent was evaporated and 5 ml of methanol and 270 mg of potassium carbonate were added to the obtained residue (7), and the mixture was stirred at room temperature for 25 minutes. The reaction mixture was poured into water, extracted with ethyl ether and dried over anhydrous magnesium sulfate. After evaporation of the solvent, the obtained residue was passed through silica gel column chromatography to obtain a dichloro derivative 8 (517 mg, 76.4%).

IR (neat): 3400, 2950, 1620, 1440 cm⁻¹.

NMR δ (CDCl₃): 5.68 (d, 1H, J=9Hz), 5.29 (m, 1H), 4.54 (m, 1H).

REFERENCE EXAMPLE 6

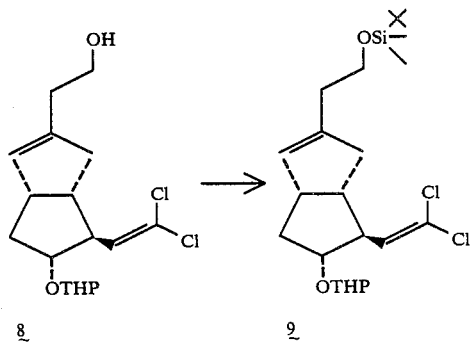

The dichloro derivative 8 (517 mg, 1.49 mmol) was dissolved in 8 ml of DMF, and then imidazole (670 mg, 9.84 mmol) and tert-butyl.dimethylsilyl chloride (810 mg, 5.37 mmol) were added thereto at room temperature and the mixture was stirred. The mixture was poured into water, extracted with toluene, washed successively with a saturated aqueous NaHCO₃ solution and a saturated saline solution, and dried over anhydrous magnesium sulfate. After evaporation of the solvent, the obtained residue was passed through silica gel column chromatography to obtain a silyl ether derivative 9 (534.1 mg, 77.8%).

IR (neat): 2950, 2850, 1620, 1465, 1260 cm⁻¹.

NMR δ (CDCl₃): 5.61 (d, J=9.0Hz, 1H), 5.65 (m, 1H), 4.50 (m, 1H), 3.11–3.99 (m, 4H), 0.90 (s, 9H), 0.05 (s, 6H).

Mass m/z: 403, 319, 301, 227, 155, 85, 55.

REFERENCE EXAMPLE 7

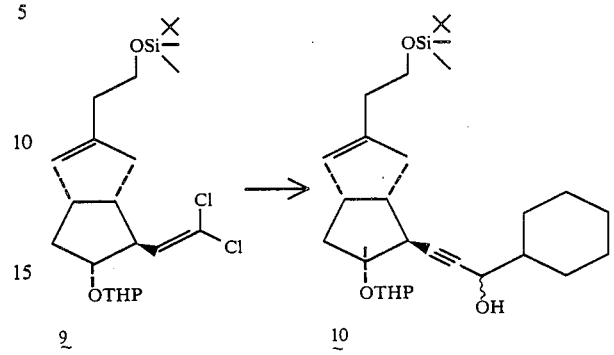

Under argon atmosphere, the silyl ether derivative 9 (178 mg, 0.39 mmol) was dissolved in 9 ml of THF, and then n-butyllithium (0.54 ml, 0.85 mmol) was added thereto at −78° C. and the mixture was stirred for 4 hours and 30 minutes. Subsequently, a solution of cyclohexanecarboxaldehyde (71.3 μm, 0.59 mmol) dissolved in 1.5 ml of THF was added thereto and the mixture was stirred for one hour. The reaction mixture was poured into a saturated aqueous NH₄Cl solution, extracted with ethyl ether, washed with water and then drired over anhydrous magnesium sulfate. After evaporation of the solvent, the obtained residue was passed through silica gel column chromatography to obtain an alcohol derivative 10 (172.5 mg, 88.1%) as colorless oily product.

IR (neat): 3410, 2925, 2225, 1450, 1255 cm⁻¹.

NMR δ (CDCl₃): 5.16 (m, 1H), 4.62–4.85 (m, 1H), 4.04 (m, 2H), 0.91 (s, 9H), 0.07 (s, 6H).

Mass m/z: 445, 427, 361, 343, 251, 159, 85, 55.

REFERENCE EXAMPLE 8

According to entirely the same procedure as in Reference example 7, the following compound 11 (55.1%) was synthesized.

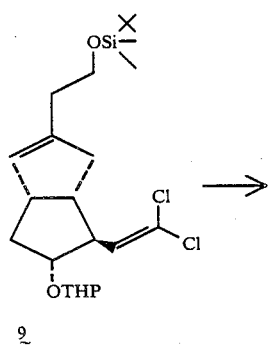

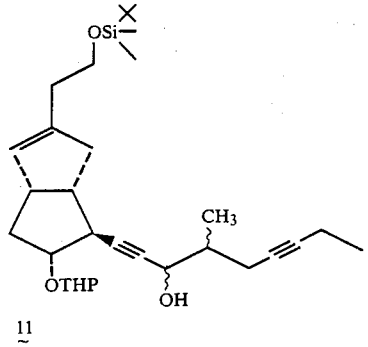

11

IR (neat): 3425, 2925, 2225, 1460, 1255 cm$^{-1}$.
NMR δ (CDCl$_3$): 5.19 (m, 1H), 4.63–4.86 (m, 1H), 0.90 (s, 9H), 0.05 (s, 6H).
Mass m/z: 496, 439, 373, 223, 131, 85, 55.

REFERENCE EXAMPLE 9

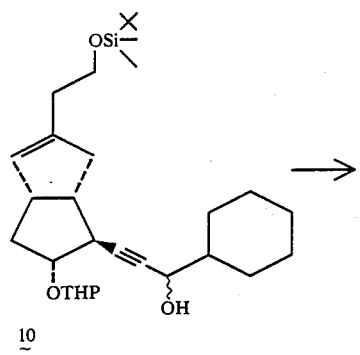

10

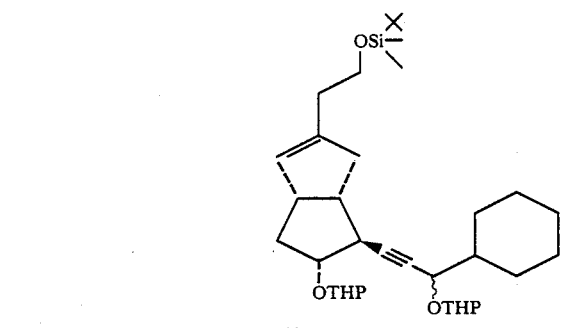

12

Under argon gas atmosphere, the alcohol derivative 10 (172 mg, 0.34 mmol) was dissolved in 3 ml of dichloromethane, and then dihydropyran (161 μl, 1.7 mmol) and catalytic amount of paratoluenesulfonic acid were added thereto at −18° C. and the mixture was stirred for 50 minutes. A saturated aqueous NaHCO$_3$ solution was added thereto, and extraction with ethyl ether was carried out. Then, the extract was washed with a saturated saline solution and dried over anhydrous magnesium sulfate. After evaporation of the solvent, the obtained residue was passed through silica gel column chromatography to obtain a triether derivative 12 (186.7 mg, 93.0%) as colorless oily product.

IR (neat): 2950, 2890, 2275, 1400, 1260, 1210 cm$^{-1}$.

NMR δ (CDCl$_3$): 5.14 (m, 1H), 4.83 (m, 2H), 4.62 (m, 1H), 0.90 (s, 9H), 0.06 (s, 6H).

REFERENCE EXAMPLE 10

According to entirely the same procedure as in Reference example 9, the following compound (76.6%) was synthesized.

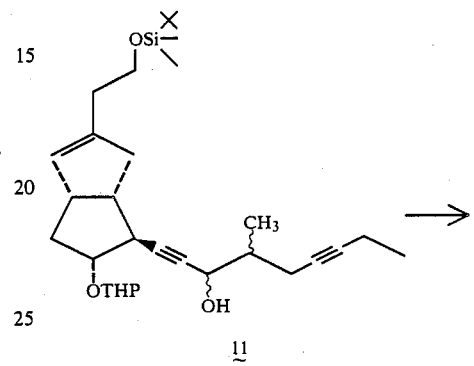

11

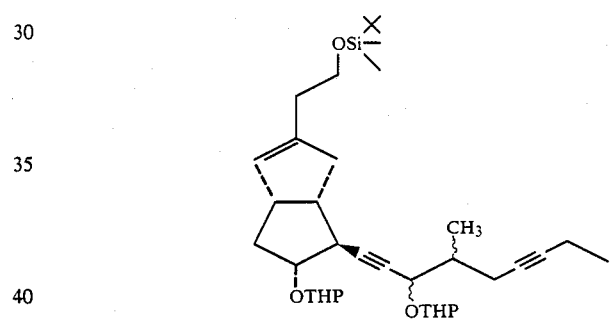

13

IR (neat): 2950, 2850, 1455, 1260, 1205 cm$^{-1}$.

NMR δ (CDCl$_3$): 5.67 (m, 1H), 4.58–5.03 (m, 2H), 0.90 (s, 9H), 0.06 (s, 6H).

REFERENCE EXAMPLE 11

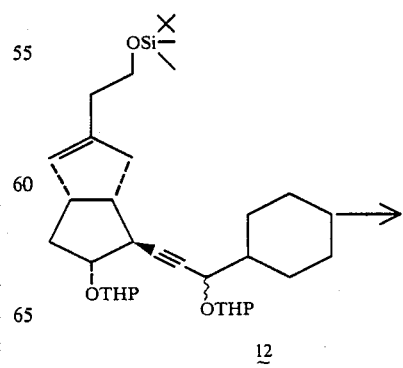

12

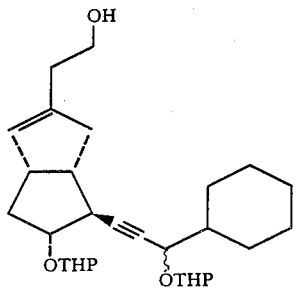

14

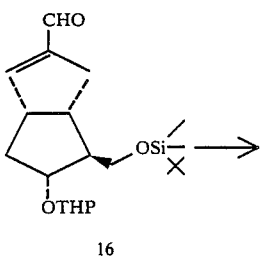

16

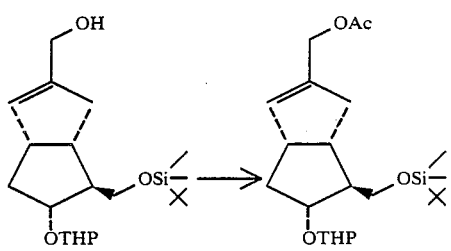

17    18

Under argon atmosphere, the triether derivative 12 (186.7 mg, 0.32 mmol) was dissolved in 5 ml of THF, and then tetrabutylammonium fluoride (0.38 ml, 0.38 mmol) was added thereto under ice cooling and the mixture was stirred at room temperature for an hour and a half. To the reaction mixture were added ethyl ether and a saturated aqueous ammonium chloride solution and the mixture was extracted with ethyl ether. The extract was washed successively with a saturated aqueous NaHCO$_3$ solution and a saturated saline soluiton, and then dried over anhydrous magnesium sulfate. After evaporation of the solvent, the obtained residue was passed through silica gel column chromatography to obtain an alcohol derivative 14 (127.3 mg, 84.6%) as colorless oily product.

IR (neat): 3425, 2925, 2850, 2225, 1450, 1200, 1120 cm$^{-1}$.

NMR δ (CDCl$_3$): 5.30 (m, 1H), 4.60–5.00 (m, 2H), 2.10–2.80 (m, 4H).

Mass m/z: 370, 286, 217, 91, 85, 43.

REFERENCE EXAMPLE 12

According to entirely the same procedure as in Reference example 11, the following compound (70.5%) was synthesized.

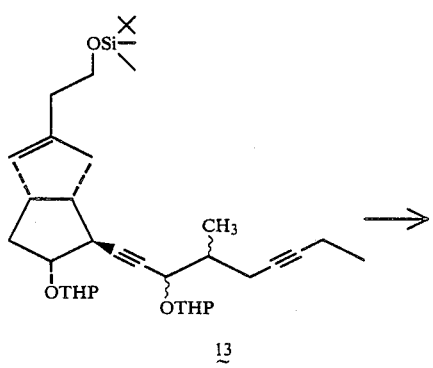

13

IR (neat): 3425, 2935, 2875, 2430, 1440, 1200 cm$^{-1}$.

NMR δ (CDCl$_3$): 5.32 (m, 1H), 4.55–5.10 (m, 2H), 0.95–1.25 (m, 6H).

Mass m/z: 382, 353, 298, 283, 223, 173, 131, 91, 85, 43.

REFERENCE EXAMPLE 13

Under argon atmosphere, 570 mg (1.5 mmol) of a starting aldehyde 16 was dissolved in 10 ml of toluene and the mixture was cooled to −78° C. 1.02 ml (1.76 Mol solution, 1.8 mmol) of diisobutylaluminum hydride was added thereto dropwise and the mixture was stirred for 30 minutes and further stirred at −20° C. for 30 minutes. Subsequently, the reaction mixture was poured into a 5% aqueous potassium hydroxide solution and extracted with ether. The crude alcohol 17 obtained by drying and condensation was dissolved in 1 ml of pyridine and then 204 mg (2.0 mmol) of acetic anhydride was added thereto under room temperature and the mixture was stirred overnight. Thereafter, the reaction solvent was evaporated under reduced pressure to obtain 630 mg (Yield: 99%) of the desired acetic acid ester 18.

NMR δ (CDCl$_3$): 5.50 (s, 1H), 4.5–4.7 (m, 3H), 2.02 (s, 3H), 0.90 (s, 9H), 0.05 (s, 6H).

REFERENCE EXAMPLE 14

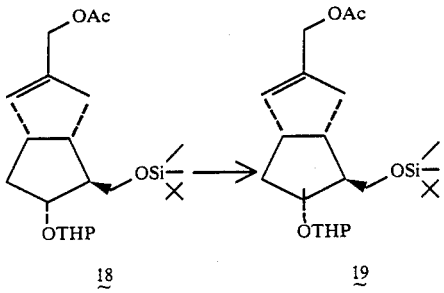

Under argon atmosphere, 630 mg (1.5 mmol) of the acetic acid ester 18 was dissolved in 10 ml of tetrahydrofuran (THF) and to a solution of 1 Mol tributylammonium fluoride in 2.25 ml of THF was added thereto at 0° C. After stirring for 4 hours, the reaction mixture was poured into ice-cold water, extracted with ether, and after drying and condensation, purified through column chromatography to obtain 438 mg (Yield: 95%) of an intended alcohol 19.

NMR δ (CDCl$_3$): 5.55 (s, 1H), 4.5–4.8 (m, 3H), 2.07 (s, 3H).

(IR (neat): 3450, 1730, 1245, 1120 cm$^{-1}$.

REFERENCE EXAMPLE 15

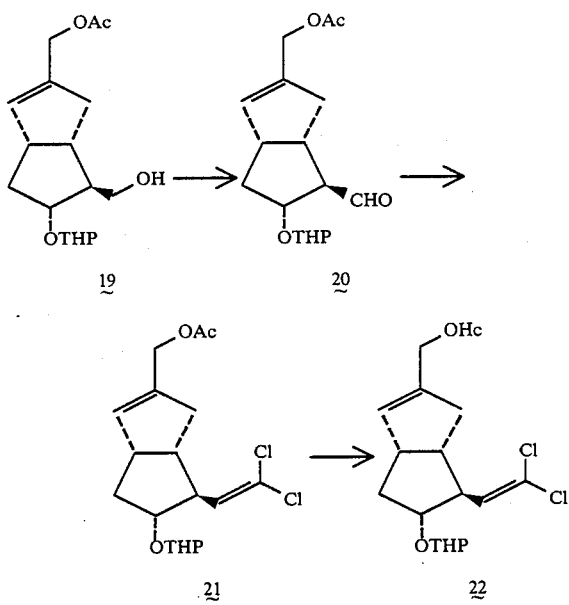

Under argon atmosphere, 217 mg (0.7 mmol) of the alcohol 19 was dissolved in a mixed solvent of 1 ml of dimethylsulfoxide and 2 ml of triethylamine and a solution of 2.34 g (14.7 mmol) of SO$_3$-pyridine complex dissolved in 3 ml of DMSO was added thereto under room temperature. After 30 minutes stirring, the reaction mixture was poured into ice-cold water, extracted with ether, dried and condensed to obtain a crude aldehyde 20.

Under argon atmosphere, 383 mg (1.5 mmol) of ethyl trichloromethylphosphonate was dissolved in a mixed solvent of 4 ml of THF and 6 ml of ether and the solution was cooled to −100° C. 0.97 ml (1.55 Mol solution, 1.5 mmol) of n-butyllithium was added thereto, and after 30 minutes, 1 ml ether solution of the above aldehyde 20. Thereafter, the temperature was gradually raised upto room temperature and after an hour, the reaction mixture was poured into ice-cold water and the solvent of ether extracted was evaporated under reduced pressure. The residue was dissolved in 2 ml of ethanol and 1 ml of a 5% aqueous potassium hydroxide solution was added thereto, and the mixture was stirred at room temperature for 30 minutes. The reaction mixture was extracted with ether, dried and condensed, and then purified through column chromatography to obtain 152 mg (Yield: 65%) of the desired dichloro derivative 22.

NMR δ (CDCl$_3$): 5.72 (d, 1H, J=9Hz), 5.47 (s, 1H), 4.5–4.7 (m, 1H), 4.10 (s, 2H).

REFERENCE EXAMPLE 16

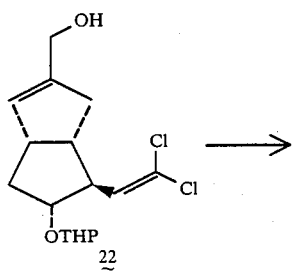

In 5 ml of dimethylformamide were dissolved 150 mg (0.45 mmol) of the dichloro derivative 22, 82 mg (0.54 mmol) of tert-butyldimethylsilyl chloride and 68 mg (1.0 mmol) of imidazole under room temperature and the solution was stirred for 1.5 hours. Thereafter, the reaction mixture was poured into ice-cold water, extracted with ether, dried and condensed, and then purified through column chromatography to obtain a silyl ether 23.

NMR δ (CDCl$_3$): 5.74 (d, 1H, J=9Hz), 5.43 (s, 1H), 4.5–4.7 (m, 1H), 4.10 (s, 2H), 0.93 (s, 9H), 0.05 (s, 6H).

REFERENCE EXAMPLE 17

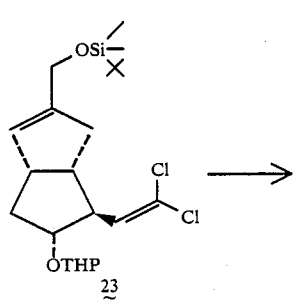

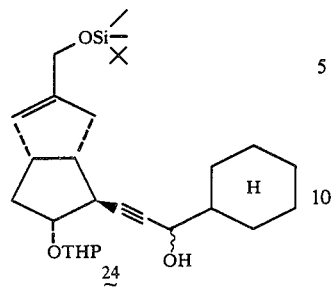

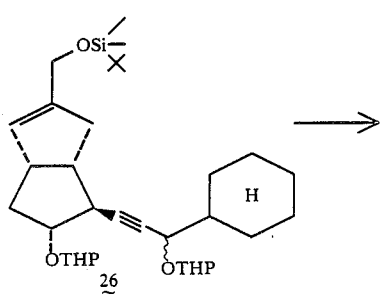

Under argon atmosphere, 189 mg (0.45 mmol) of the silyl ether 23 was dissolved in 8 ml of THF and the solution was cooled to −78° C. 0.63 ml (1.56 Mol solution, 0.99 mmol) of n-butyllithium was added thereto and the mixture was stirred for 3 hours. Thereafter, cyclohexanecarboxylaldehyde was added thereto and the mixture was stirred for further 3 hours, poured into ice-cold water and extracted with ether. After drying and condensation, the residue was purified through silica gel column chromatography to obtain 121 mg (Yield: 58%) of the desired alcohol derivative 24.

NMR δ (CDCl$_3$): 5.36 (s, 1H), 4.5–5.0 (m, 1H), 4.05 (s, 2H), 0.90 (s, 9H), 0.05 (s, 6H).

IR (neat): 3420, 1450, 1075, 835 cm$^{-1}$.

REFERENCE EXAMPLE 18

According to the same procedure as in Reference example 17, the following compound 25 (35%) was synthesized.

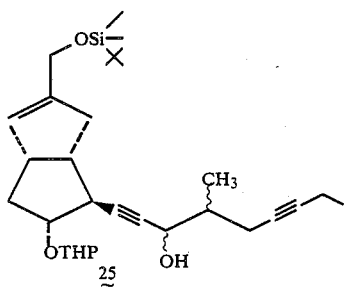

NMR δ (CDCl$_3$): 5.38 (s, 1H), 4.5–4.9 (m, 1H), 4.05 (s, 2H), 0.90 (s, 9H), 0.05 (s, 6H).

IR (neat): 3400, 2220, 1455, 1075, 1035 cm$^{-1}$.

REFERENCE EXAMPLE 19

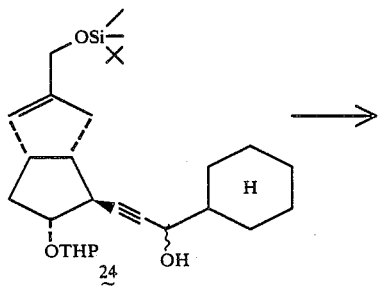

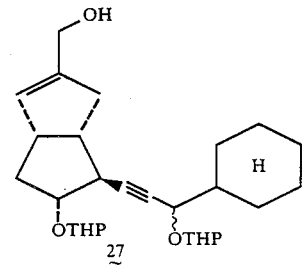

In 10 ml of methylene chloride were dissolved 115 mg of the alcohol derivative 24 and 20 mg of dihydropyran, and under room temperature, 1 mg of p-toluenesulfonic acid was added thereto and the mixture was stirred for an hour. The reaction mixture was poured into an aqueous sodium hydrogen carbonate solution, extracted with ether, condensed and purified simply through column chromatography to obtain crude triether derivative 26. This product was dissolved in 5 ml of THF, and at rrom temperature, 0.5 ml (1 Mol THF solution, 0.5 mmol) of tetra-n-butylammonium fluoride was added thereto and the mixture was stirred for 5 hours. Thereafter, the reaction mixture was poured into ice-cold water, extracted with ether, dried and condensed, and then purified through column chromatography to obtain 83 mg (Yield: 73%) of the desired alcohol 27.

NMR δ (CDCl$_3$): 5.57 (s, 1H), 4.6–5.0 (m, 2H), 4.05 (s, 2H).

IR (neat): 3430 (broad), 1450, 1130, 1020 cm$^{-1}$.

EXAMPLE 1

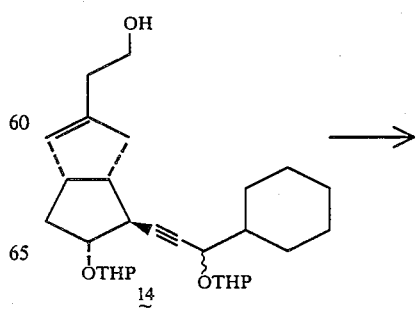

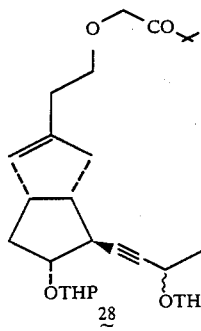

Under argon gas atmosphere, the alcohol derivative 14 (127 mg, 0.27 mmol) was dissolved in 3.5 ml of dichloromethane, and tert-butyl bromoacetate (1.32 ml, 8.1 mmol) and 1.8 ml of a 50 % NaOH were added thereto at room temperature and the mixture was vigorously stirred. Further, catalytic amount of tetra-n-butylammonium bisulfate was added thereto and the mixture was stirred for 24 hours. Water was added thereto and the reaction mixture was extracted with ethyl ether, washed with water and dried over anhydrous magnesium sulfate. After evaporation of the solvent, the obtained residue was passed through silica gel column chromatography to obtain the ester derivative 28 (158 mg, 100%) as colorless oily product.

IR (neat): 3400, 2925, 2850, 1755, 1445, 1365, 1135 cm$^{-1}$.

NMR δ (CDCl$_3$): 5.28 (m, 1H), 4.93 (m, 1H), 4.68 (m, 1H), 4.06 (s, 2H), 1.50 (s, 9H).

EXAMPLE 2

According to entirely the same procedure as in Example 1, the following compound (65.7 mg, 100%) was synthesized.

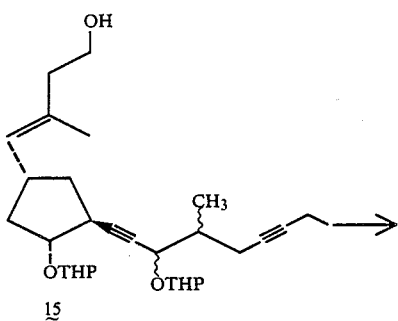

IR (neat): 3450, 2940, 2230, 1750, 1450, 1365 cm$^{-1}$.

NMR δ (CDCl$_3$): 5.30 (m, 1H), 4.92 (m, 1H), 4.68 (m, 1H), 4.06 (s, 2H), 1.50 (s, 9H).

EXAMPLE 3

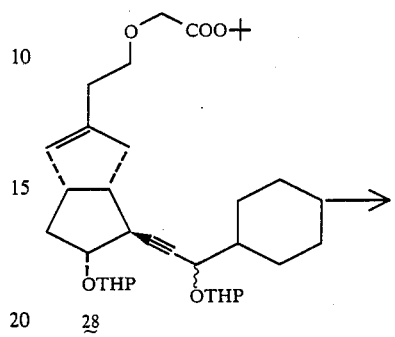

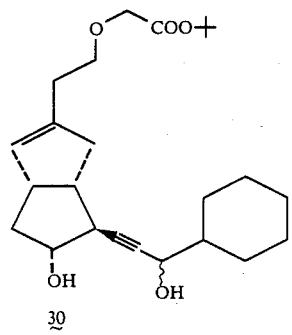

Under argon atmosphere, the tetrahydropyranyl ether derivative 28 (158 mg, 0.27 mmol) was dissolved in 0.4 ml of THF, 5 ml of a 65% acetic acid was added thereto and the mixture was stirred at 50° C. for 2 hours and 30 minutes. Ethyl acetate was added thereto, and the reaction mixture was poured into a saturated aqueous NaHCO$_3$ solution, extracted with ethyl acetate and washed with water. The extract was dried over anhydrous magnesium sulfate, and after evaporation of the solvent, the obtained residue was passed through silica gel column chromatography to obtain the dialcohol derivative 30 (91.7 mg, 81.2%) as colorless oily product.

IR (neat): 3425, 2950, 2860, 1750, 1450, 1370, 1140 cm$^{-1}$.

NMR δ (CDCl$_3$): 5.34 (m, 1H), 3.91 (s, 2H), 3.45-3.75 (m, 4H), 1.50 (s, 9H).

Mass m/z: 400, 344, 276, 224, 186, 85, 57.

EXAMPLE 4

According to entirely the same procedure as in Example 3, the following compound 31 (74.8%) was synthesized.

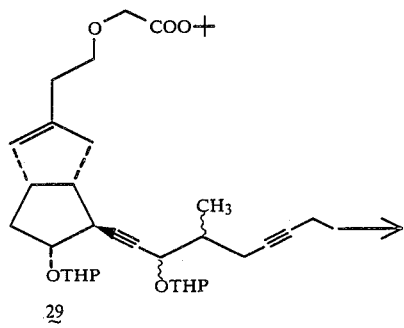

29

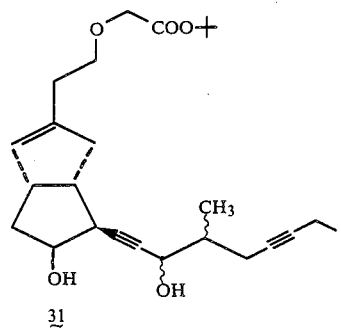

31

IR (neat): 3350, 2920, 2870, 1745, 1365 cm⁻¹.
NMR δ (CDCl₃): 5.30 (m, 1H), 4.35 (m, 1H), 3.88 (s, 2H), 3.45–3.70 (m, 4H), 1.50 (s, 9H), 1.00–1.23 (m, 6H).
Mass m/z: 374, 327, 251, 223, 131, 85, 57.

EXAMPLE 5

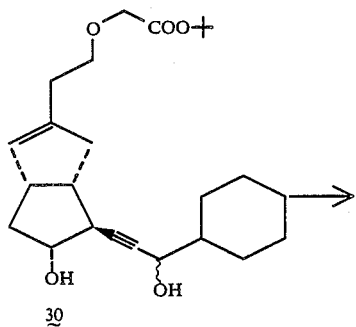

30

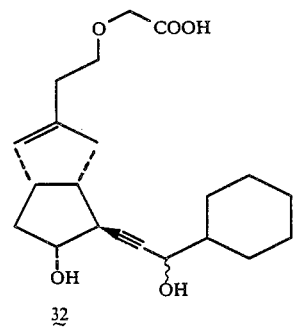

32

The dialcohol derivative 30 (91.7 mg, 0.22 mmol) was dissolved in 2.5 ml of ethanol, and 1.65 ml of a 5% KOH was added thereto at room temperature and the mixture was stirred for an hour. The mixture was carefully neutralized with a 5N-hydrochloric acid and adjusted pH to 3-4, and extracted with ethyl acetate. After drying over anhydrous magnesium sulfate, the solvent was evaporated and the obtained residue was passed through neutral silica gel capillary column to obtain the carboxylic acid derivative 32 (31.8 mg, 40.1%) as colorless oily product.

IR (neat): 3350, 2925, 2850, 2220, 1710, 1410, 1270 cm⁻¹.

NMR δ (CDCl₃): 5.45 (m, 1H), 4.13 (m, 2H), 4.08 (d, J=7.2Hz, 2H), 3.65 (m, 2H), 3.19 (m, 1H).

Mass m/z: 344, 261, 235, 131, 83, 55.

EXAMPLE 6

According to entirely the same procedure as in Example 5, the following compound 33 (7.4 mg, 24.0%) was prepared.

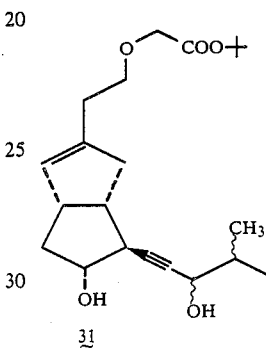

31

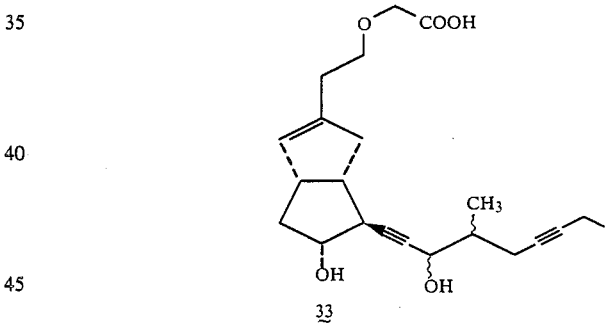

33

IR (neat): 3350, 2910, 2415, 1720, 1115 cm⁻¹.
NMR δ (CDCl₃): 5.45 (m, 1H), 4.10–4.45 (m, 2H), 4.08 (d, J=7.3Hz, 2H), 3.64 (m, 2H), 3.20 (m, 1H), 1.10 (m, 6H).
Mass m/z: 355, 281, 207, 149, 73, 44.

EXAMPLE 7

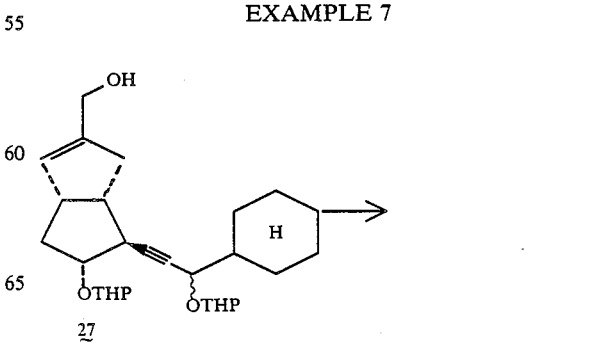

27

-continued

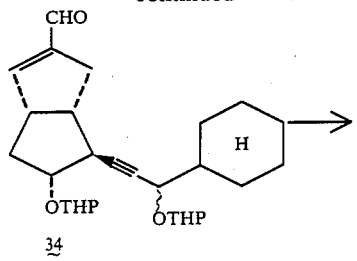
34

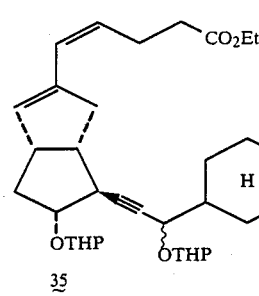
35

83 mg of the alcohol 27 (83 mg, 0.18 mmol) was dissolved in a mixed solvent of 0.5 ml of DMSO and 0.8 ml of triethylamine and a solution of 605 mg (3.8 mmol) of $SO_3$-pyridine complex dissolved in 2 ml of DMSO was added thereto. After stirring for 20 minutes, the mixture was poured into ice-cold water, extracted with ether, dried and condensed to obtain crude aldehyde 34.

In 2 ml of DMSO was suspended 21.6 mg (0.54 mmol) of sodium hydride and the suspension was stirred at 50° C. for 30 minutes. After the reacted solution was cooled to room temperature, solution of 247 mg (0.54 mmol) of 3-ethoxycarbonylpropyltriphenylphosphonium bromide dissolved in 2 ml of DMSO was added thereto. After stirring for 15 minutes, the above-mentioned aldehyde 34 was added thereto and the mixture was stirred for an hour. The reaction mixture was poured into ice-cold water, extracted with ether, dried and condensed, and then purified through thin layer chromatography to obtain 61 mg (Yield: 61%) of the desired ester 35.

NMR δ (CDCl$_3$): 5.90 (d, 1H, J=12Hz), 5.48 (s, 1H), 5.3–5.5 (m, 1H), 4.6–5.1 (m, 2H), 4.08 (q, 2H, J=7Hz), 1.26 (t, 3H, J=7Hz).

IR (neat): 1730, 1135, 1020, 735 cm$^{-1}$.

EXAMPLE 8

According to entirely the same procedure as in Example 7, the following compound 36 (73%) was synthesized.

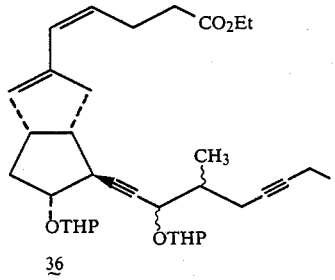
36

NMR δ (CDCl$_3$): 5.98 (d, 1H, J=12Hz), 5.45 (s, 1H), 5.1–5.4 (m, 1H), 4.5–5.1 (m, 2H), 4.08 (q, 2H, J=7Hz).

IR (neat): 2230, 1735, 1450, 1020 cm$^{-1}$.

EXAMPLE 9

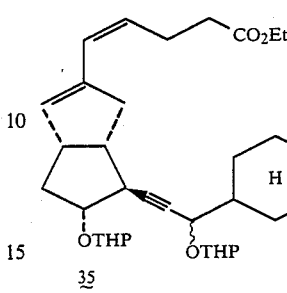
35

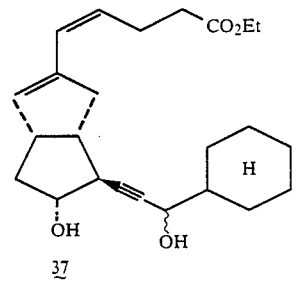
37

59 mg of the ester 35 (0.106 mmol) was dissolved in an aqueous 65% acetic acid solution and the solution was heated and stirred at 50° C. for 1.5 hours. After cooling, the mixture was poured into an aqueous sodium hydrogen carbonate solution, extracted with ethyl acetate, dried and condensed, and then purified through thin layer chromatography to obtain 34 mg (Yield: 87%) of the desired diol 37.

NMR δ (CDCl$_3$): 5.88 (d, 1H, J=12Hz), 5.48 (s, 1H), 5.1–5.4 (m, 1H), 4.05 (q, 2H, J=7Hz), 1.23 (t, 3H, J=7Hz).

IR (neat): 3380, 1730, 1160, 1095 cm$^{-1}$.

EXAMPLE 10

According to the same procedure as in Example 9, the following compound 38 (71%) was synthesized.

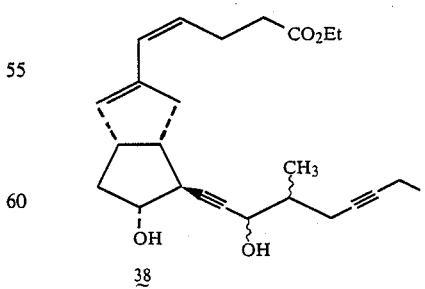
38

NMR δ (CDCl$_3$): 5.86 (d, 1H, J=12Hz), 5.47 (s, 1H), 5.1–5.4 (m, 1H), 4.05 (q, 2H, J=7Hz), 1.0–1.4 (m, 9H).

IR (neat): 3350, 1725, 1445, 1025 cm$^{-1}$.

EXAMPLE 11

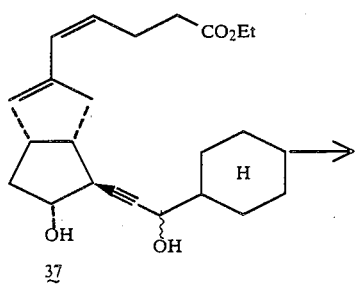

34 mg of the diol 37 was dissolved in 2 ml of ethanol and 1 ml of a 5% aqueous potassium hydroxide solution was added thereto under room temperature and the mixture was stirred for 1.5 hours. Thereafter, the mixture was carefully neutralized with a 1% hydrochloric acid and extracted with ethyl acetate. After drying and condensation, the residue was purified by neutral silica gel column chromatography to obtain 30 mg (Yield: 97%) of the carboxylic acid 39.

NMR δ (CDCl$_3$): 6.01 (d, 1H, J=12Hz), 5.60 (s, 1H), 5.3–5.5 (m, 1H), 4.0–4.3 (m, 3H).

IR (neat): 3320, 1705, 1260, 1085 cm$^{-1}$.

Mass m/e: 358 (M$^+$), 340, 322.

EXAMPLE 12

According to the same procedure as in Example 11, The following compound 40 (100%) was synthesized.

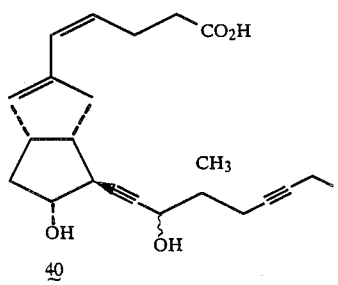

NMR δ (CDCl$_3$): 5.98 (d, 1H, J=12Hz), 5.57 (s, 1H), 5.3–5.5 (m, 1H), 1.0–1.3 (m, 6H).

IR (neat): 3350, 2240, 1710, 1090, 1020 cm$^{-1}$.

Mass m/e: 370 (M$^+$), 352, 334.

(PREPARATION OF PHARMACEUTICAL)

EXAMPLE 13

5 mg of 3-oxa-13,14,18,18,19,19-hexahydro-16,20-dimethyl-9(0)-methano-Δ$^{6(9\alpha)}$-prostaglandin I$_1$ dissolved in 5 ml of ethanol, 0.2 g of carboxymethylcellulose calcium, 20 mg of silicon dioxide, 0.2 g of magnesium stearate and 5 g of mannitol were mixed and dried according to a conventional method. Thereafter, the mixture was made up to 10 g with addition of mannitol and then mixed sufficiently until it became uniform. The resulting mixture was directly punched by use of a mortar and a pounder according to a conventional manner to obtain 100 tablets containing 50 μg of the active substance in one tablet.

EXAMPLE 14

According to the same procedures as in Example 13 except that 3-oxa-13,14,18,18,19,19-hexahydro-17,20-dimethyl-9(0)-methano-Δ$^{6(9\alpha)}$-prostaglandin I$_1$ and 4,5,13,14,18,18,19,19-octadehydro-16,20-dimethyl-9(0)-methano-Δ$^{6(9\alpha)}$-prostaglandin I$_1$ were employed, 100 tablets containing 50 μg of the active substance in one tablet were obtained.

EXAMPLE 15

70 mg of α-cyclodextrin inclusion compound of 3-oxa-13,14,18,18,19,19-hexahydro-16,20-dimethyl-9(0)-methano-Δ$^{6(9\alpha)}$-prostaglandin I$_1$, 0.2 g of carboxymethyl cellulose calcium, 20 mg of silicon dioxide, 0.2 g of magnesium stearate and dried mannitol were added such that the mixture was made up to 10 g and then mixed sufficiently until it became uniform. The resulting mixture was direclty punched according to a conventional method to obtain 100 tablets containing 50 μg of the active substance in one tablet.

EXAMPLE 16

70 mg of α-cyclodextrin comopound of 3-oxa-13,14,18,18,19,19-hexahydro-16,20-dimethyl-9(0)-methano-Δ$^{6(9\alpha)}$-prostaglandin I$_1$, 0.23 g of magnesium stearate and lactose were added such that the mixture was made up to 2.3 g and then mixed sufficiently until it became uniform. The resulting mixture was charged into a gelatin capsule No. 3 according to a conventional method to obtain 100 capsules wherein 50 μg of the active substance was contained in one capsule.

EXAMPLE 17

14 mg of α-cyclodextrin inclusion compound of 3-oxa-13,14,18,18,19,19-hexahydro-16,20-dimethyl-9(0)-methano-Δ$^{6(9\alpha)}$-prostaglandin I$_1$ was dissolved in 100 ml of a distilled water. The resulting solution was sterilized according to a conventional method and 1 ml of the solution was injected into ampoules of 5 ml capacity to obtain 100 injection preparations containing 10 μg of the active substance in one ampoule.

(PHYSIOLOGICAL ACTIVITY)

EXPERIMENT 1

Platelet aggregation inhibiting effect (Method of experiment)

Bloods were sampled from healthy male adults (22 to 34 years old) with no administration of drug for 2 weeks early in the morning when they were hungry. By use of an injector filled with a 3.8% sodium citrate solution, 50 ml of blood was sampled, immediately stirred by turning upside down and centrifuged at 200 G for 15 minutes. The supernatant was separated as the PRP (platelet rich plasma) and the residue was further subjected to centrifugation at 2000 G for 15 minutes, followed by recovery of the supernatant as PPP (poor platelet plasma) which ws provided for use in the experiment. 250 μl of PRP was placed in a cuvette, 5 μl of an 1% aqueous ethanol solution of the compound of the present invention or an 1% acqueous ethanol solution was added, and incubation was carried out at 37° C. for one minute. Then, an aggregation inducing agent (ADP) was added and the process of aggregation was recorded by Aggregometer (produced by Sienco Co.). As the concentration of ADP, the minimum concentrations of ADP (2 to 10 μM) to give the maximum aggregation for respective platelets were employed. The inhibition percentage of platelet aggregation was calculated by the following formula:

Inhibition percentage = (A − B/A) × 100

A: Maximum aggregation ratio during addition of solvent (5% aqueous ethanol solution)
B: Maximum aggregation ratio during addition of the compound of the present invention.

The platelet aggregation inhibiting effects of the compounds of the present invention are shown in terms of $IC_{50}$ values in Table 1.

TABLE 1

Human platelet aggregation inhibiting effect (in vitro)

| Compound | Platelet aggregation inhibiting ratio ($IC_{50}$) |
|---|---|
| [structure with COOH, CH₃, alkyne] | $1.5 \times 10^{-9}$ M |
| [structure with COOH, cyclohexyl, H] | $1.0 \times 10^{-8}$ M |
| [structure with COOH-O-, CH₃, alkyne] | $1.9 \times 10^{-9}$ M |

TABLE 1-continued

Human platelet aggregation inhibiting effect (in vitro)

| Compound | Platelet aggregation inhibiting ratio ($IC_{50}$) |
|---|---|
| [structure with COOH-O-, cyclohexyl, H] | $4.5 \times 10^{-9}$ M |
| OP-41483 | $1.2 \times 10^{-8}$ M |

EXPERIMENT 2

Antiulcer effect (Method of experiment)

Male wistar strain rats (weighing 250–280 g) were fasted for 18 hours and subjected to peritoneotomy under ether anesthesia for ligature of pylorus, and after 4 hours under abstinence from food and water, gastric juice was sampled. The gastric juice was centrifuged at 3000 rpm for 10 minutes, and then the amount, pH and acidity of the gastric juice were measured. The acidity was measured by titration bymeans of an automatic titrating device (produced by Toa Denpa Kogyo) with a 0.1 N NaOH to pH 7.0 and calculated according to the following formula:

$$\frac{\text{Titration amount (0.1 N NaOH) required for 1 ml sample}}{\text{Titration amount (0.1 N NaOH) required for 1 ml 0.1 N HCl}} \times 0.1 \text{ (N)} \times 1000 \text{ (mEq/l)}$$

The gastric juice secretion inhibition percentage was calculated according to the following formula:

$$\text{Inhibition percentage} = \frac{A - B}{A} \times 100$$

A: Amount of gastric acid excreted in Control group
B: Amount of gastric acid excreted in Drug group.

The drugs to be tested were administered subcutaneously immediately after pylorus ligature. The results are shown in Table 2.

TABLE 2

Rat secreted gastric acid inhibiting effect

| Compound | Dose (μg/kg, s.c.) | Amount of gastric acid secreted (mEq/l) | Inhibition percentage (%) |
|---|---|---|---|
| (structure 1) | 100 | 21.3 ± 8.4 | 71.1 |
| (structure 2) | 100 | 68.4 ± 10.1 | 7.1 |
| (structure 3) | 100 | 29.7 ± 9.5 | 59.6 |
| (structure 4) | 100 | 84.9 ± 10.8 | 0 |
| Solvent | | 73.6 ± 4.3 | |

We claim:

1. A pharmaceutical having circulation ameliorating effect and antiulcer effect and comprising an effective amount of prostacyclins represented by the formula [I]:

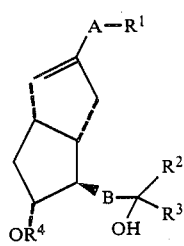

wherein $R^1$ represents $-CO_2R^5$ group (in the group, $R^5$ represents a hydrogen atom, or a straight or branched alkyl group having 1 to 12 carbon atoms, or an aralkyl group having 7 to 12 carbon atoms, or a cycloalkyl group having 4 to 7 carbon atoms which may be unsubstituted or substituted by at least one alkyl group having 1 to 4 carbon atoms, an unsubstituted phenyl group, a phenyl group substituted by at least one selected from the group consisting of a halogen atom, a hydroxy group, an acyloxy group having 2 to 7 carbon atoms, an alkyl group having 1 to 4 carbon atoms which may be substituted by a halogen atom, an alkoxy group having 1 to 4 carbon atoms which may be substituted by a halogen atom, a nitrile group, a carboxy group or an alkoxycarbonyl group having 2 to 7 carbon atoms, or a monoequivalent cation), or $-CONR^6R^7$ group (in the group, $R^6$ and $R^7$ each may be the same or different, represents a hydrogen atom, an alkyl group having 1 to 10 carbon atom, or an unsubstituted 5- or 6-membered ring combined with nitrogen atom bonded thereto which may have further hetero atoms or a 5- or 6-membered ring combined with nitrogen atom bonded thereto which may have further hetero atoms and substituted by at least one selected from an alkyl group having 1 to 4 carbon atoms which may be substituted by a halogen atom); A represents $-CH=CH-CH_2CH_2-$;

B represents $-C\equiv C-$ group; $R^2$ represents a straight or branched alkyl group; having 3 to 10 carbon atoms, a cycloalkyl group having 4 to 7 carbon atoms which may be unsubstituted or substituted by at least one alkyl group having 1 to 4 carbon atoms, or a straight or branched alkenyl group having 3 to 12 carbon atoms, or a straight or branched alkynyl group having 3 to 8 carbon atoms, or a substituted alkyl group having 1 to 3 carbon atoms which is substituted by a phenyl group or a phenoxy group which may be substituted by at least one as mentioned for substituents for $R^5$, or an alkoxy group having 1 to 6 carbon atoms, or a cycloalkyl group having 5 to 8 carbon atoms; $R^3$ represents a hydrogen atom, a methyl group or a vinyl group; $R^4$ represents a hydrogen atom, or an acyl group having 1 to 7 carbon atoms, a tri(1 to 7 carbon atoms)hydrocarbyl-silyl group or a group forming an acetal bond with an oxygen atom of a hydroxy group; a double bond in the substituent represented by A is E or Z, or a mixture thereof; asymmetric center in the substituent represented by $R^2$ is an R-configuration or S-configuration, or a mixture thereof, or non-toxic salt of its acid, or their cyclodextrin-inclusion compound in admixture with an inert carrier or excipient.

2. A method of treating circulatory and ulcer ailments in a subject, which comprises administering to said subject an effective amount of the prostacyclin of claim 1.

* * * * *

UNITED STATES PATENT AND TRADEMARK OFFICE
CERTIFICATE OF CORRECTION

PATENT NO. : 4,839,388
DATED : June 13, 1989
INVENTOR(S) : Masakatsu SHIBASAKI, et al It is certified that error appears in the above-identified patent and that said Letters Patent is hereby corrected as shown below:

On the title page, under item [19], "Sibasaki et al." should read --Shibasaki--
On the Title Page, Item [75], the first inventor's last name is incorrect, it should read as follows:

--Masakatsu SHIBASAKI--

Signed and Sealed this

Seventeenth Day of April, 1990

Attest:

HARRY F. MANBECK, JR.

*Attesting Officer*      *Commissioner of Patents and Trademarks*